(12) United States Patent
McLaughlin et al.

(10) Patent No.: US 10,526,264 B2
(45) Date of Patent: Jan. 7, 2020

(54) OXY-COPE REARRANGEMENT FOR THE MANUFACTURE OF INSECTICIDAL CYCLOPENTENE COMPOUNDS

(71) Applicant: BASF SE, Ludwigshafen am Rhein (DE)

(72) Inventors: Martin John McLaughlin, Ludwigshafen (DE); Karsten Koerber, Ludwigshafen (DE); Birgit Gockel, Ludwigshafen (DE); Pascal Bindschaedler, Limburgerhof (DE); Sebastian Soergel, Limburgerhof (DE); Devendra Vyas, Navi Mumbai (IN); Johannes Roeckl, Nierstein (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 16/315,417

(22) PCT Filed: Jun. 23, 2017

(86) PCT No.: PCT/EP2017/065610
§ 371 (c)(1),
(2) Date: Jan. 4, 2019

(87) PCT Pub. No.: WO2018/007175
PCT Pub. Date: Jan. 11, 2018

(65) Prior Publication Data
US 2019/0308920 A1 Oct. 10, 2019

(30) Foreign Application Priority Data

Jul. 7, 2016 (IN) .............................. 201621023277
Aug. 30, 2016 (EP) ..................................... 16186257

(51) Int. Cl.
C07C 33/00 (2006.01)
C07C 17/00 (2006.01)
(Continued)

(52) U.S. Cl.
CPC ........ C07C 33/486 (2013.01); C07C 17/2635 (2013.01); C07C 25/24 (2013.01);
(Continued)

(58) Field of Classification Search
CPC ... C07C 33/486; C07C 17/2635; C07C 25/24; C07C 45/512; C07C 63/74
See application file for complete search history.

(56) References Cited

FOREIGN PATENT DOCUMENTS

WO 2015075174 A1 5/2015
WO 2015104422 A1 7/2015
(Continued)

OTHER PUBLICATIONS

European Search Report for EP Patent Application No. 16186257.8, dated Feb. 17, 2017, 3 pages.
(Continued)

Primary Examiner — Sikarl A Witherspoon
(74) Attorney, Agent, or Firm — Brinks Gilson & Lione

(57) ABSTRACT

Compounds of formula I

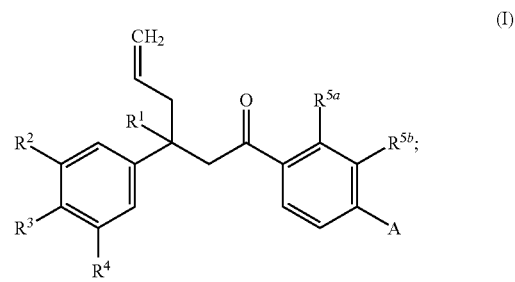

a process for preparation of compounds of formula I; precursor compounds of formula II

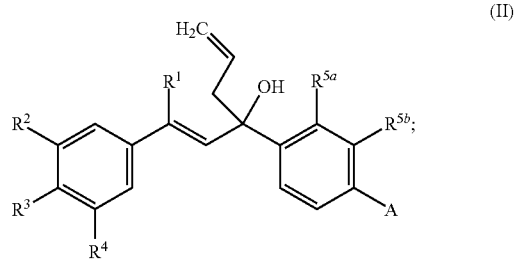

a process for preparation of precursor compounds of formula II; compounds of formula III

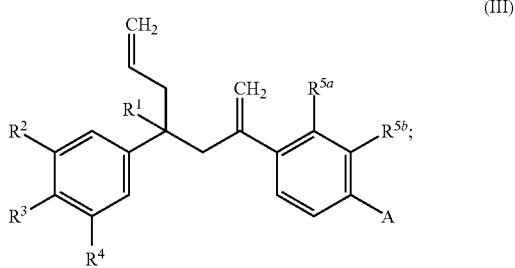

a process for the preparation of compounds of formula IV from compounds of formula III
(Continued)

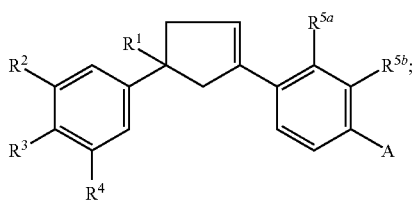

(IV)

and the use of compounds of formula I for the preparation of compounds of formula IV.

18 Claims, No Drawings

(51) Int. Cl.
  *C07C 25/00* (2006.01)
  *C07C 45/00* (2006.01)
  *C07C 63/00* (2006.01)
  *C07C 33/48* (2006.01)
  *C07C 49/813* (2006.01)
  *C07C 45/51* (2006.01)
  *C07C 63/74* (2006.01)
  *C07C 17/263* (2006.01)
  *C07C 25/24* (2006.01)

(52) U.S. Cl.
  CPC .......... *C07C 45/512* (2013.01); *C07C 49/813* (2013.01); *C07C 63/74* (2013.01)

(56) References Cited

FOREIGN PATENT DOCUMENTS

| WO | 2015114157 A1 | 8/2015 |
| WO | 2015128358 A1 | 9/2015 |
| WO | 2015169883 A1 | 11/2015 |
| WO | 2015189080 A1 | 12/2015 |
| WO | 2016016369 A1 | 2/2016 |
| WO | 2016055431 A1 | 4/2016 |
| WO | 2016059240 A1 | 4/2016 |
| WO | 2016071499 A1 | 5/2016 |
| WO | 2016091674 A1 | 6/2016 |
| WO | 2016102482 A1 | 6/2016 |
| WO | 2016102488 A1 | 6/2016 |
| WO | 2016102490 A1 | 6/2016 |
| WO | 2016113261 A1 | 7/2016 |
| WO | 2016113271 A1 | 7/2016 |
| WO | 2016128239 A1 | 8/2016 |
| WO | 2016128240 A1 | 8/2016 |
| WO | 2016128261 A2 | 8/2016 |
| WO | 2016180833 A1 | 11/2016 |
| WO | 2017001252 A1 | 1/2017 |
| WO | 2017012938 A1 | 1/2017 |
| WO | 2017016883 A1 | 2/2017 |
| WO | 2017025454 A1 | 2/2017 |
| WO | 2017032580 A1 | 3/2017 |
| WO | 2017045955 A1 | 3/2017 |
| WO | 2017055386 A1 | 4/2017 |
| WO | 2017133942 A1 | 8/2017 |
| WO | 2017140563 A1 | 8/2017 |
| WO | 2017140614 A1 | 8/2017 |
| WO | 2017153217 A1 | 9/2017 |
| WO | 2017153218 A1 | 9/2017 |
| WO | 2017167832 A1 | 10/2017 |
| WO | 2018007175 A1 | 1/2018 |
| WO | 2018011056 A1 | 1/2018 |
| WO | 2018015843 A1 | 1/2018 |
| WO | 2018041665 A1 | 3/2018 |

OTHER PUBLICATIONS

International Search Report for PCT Patent Application No. PCT/EP2017/065610, dated Jul. 18, 2017, 3 pages.

Jung, et al., "Versatile Diastereoselectivity in Formal [3,3]-Sigmatropic Shifts of Substituted 1-Alkenyl-3-alkylidenecyclobutanols and Their Silyl Ethers", Journal of the American Chemical Society, vol. 127, Issue 32, 2005, pp. 11206-11207.

Pohmakotr, et al., "Anwendungen der Magnesiumderivate von Thioacrolein-Dianionen zur Synthese schwefelfreier Verbindungen (Vinyl-und Divinylepoxide, Acylcyclopentene)", Chemische Berichte, vol. 112, Issue 4, Apr. 1979, pp. 1420-1439.

OXY-COPE REARRANGEMENT FOR THE MANUFACTURE OF INSECTICIDAL CYCLOPENTENE COMPOUNDS

This application is a National Stage application of International Application No. PCT/EP2017/065610, filed Jun. 23, 2017. This application also claims priority under 35 U.S.C. § 119 to European Patent Application No. 16186257.8, filed Aug. 30, 2016 and to Indian Patent Application No. 201621023277, filed Jul. 7, 2016.

The invention relates to compounds of formula I

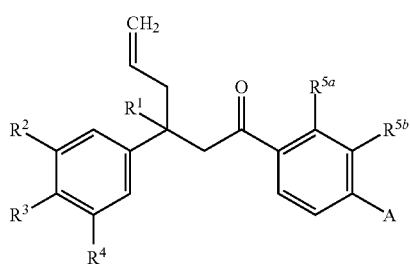

wherein $R^1$ is halomethyl;

$R^2$ is halogen, halomethyl, or halomethoxy;

$R^3$, $R^4$ are independently H, or as defined for $R^2$;

$R^{5a}$ is H, $C_1$-$C_4$-alkyl, or $C_1$-$C_4$-haloalkyl;

$R^{5b}$ is CN, halogen, $C_1$-$C_2$-alkyl, $C_1$-$C_2$-haloalkyl, $C_1$-$C_2$-alkoxy, $C_1$-$C_2$-haloalkoxy; or $R^{5a}$ and $R^{5b}$ form together with the C-atoms they are bound to a 5-, or 6-membered saturated, partially, or fully unsaturated ring containing none, or one heteroatom O, $N(O)_n$ or $S(O)_m$ as ring members;

A is halogen, CN, $C_1$-$C_6$-alkoxy, $C_6$-$C_{10}$-aryloxy, $C_1$-$C_6$-haloalkoxy, $C_6$-$C_{10}$-arylalkoxy, $C_6$-$C_{10}$-aryl-$C_1$-$C_6$-alkoxy, $OS(O)_2R^6$; or a group $A^1$, or $A^2$; wherein $A^1$ is a group of following formula:

wherein

\# denotes the attachment point to the remainder of the molecule;

Y $OR^7$, or $N(R^8)R^9$; and $A^2$ is a group of following formula:

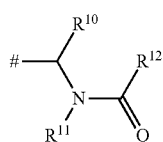

wherein

\# denotes the attachment point to the remainder of the molecule;

$R^6$ halogen, $C_1$-$C_6$-alkyl, $C_1$-$C_6$-haloalkyl;

phenyl, which is unsubstituted, or substituted with halogen, OH, CN, $NO_2$, $C_1$-$C_6$-alkyl, or $C_1$-$C_6$-haloalkyl;

$R^7$ a) H;

b) $C_1$-$C_6$-alkyl, $C_1$-$C_6$-haloalkyl, $C_1$-$C_6$-alkenyl, $C_1$-$C_6$-alkynyl, $C_1$-$C_6$-alkoxy-$C_1$-$C_6$-alkyl; or c) phenyl or benzyl, which are unsubstituted, or substituted by halogen, $C_1$-$C_2$-alkyl, $C_1$-$C_2$-haloalkyl, or $C_1$-$C_2$-alkoxy;

$R^8$ H, CN;

$C_1$-$C_6$-alkyl-C(=O), $C_1$-$C_6$-haloalkyl-C(=O), $C_1$-$C_6$-alkyl-OC(=O), $C_1$-$C_6$-alkenyl-OC(=O), or $C_6$-$C_{12}$-aryl-$C_1$-$C_6$-alkyl-OC(=O);

$C_1$-$C_{10}$-alkyl, $C_3$-$C_8$-cycloalkyl, $C_2$-$C_{10}$-alkenyl, $C_2$-$C_{10}$-alkynyl, which are unsubstituted, or substituted by $R^{81}$;

$R^{81}$ halogen, CN, $N_3$, $NO_2$, SCN, $SF_5$, $C_3$-$C_8$-cycloalkyl, $C_3$-$C_8$-halocycloalkyl, $C_1$-$C_6$-alkoxy, $C_1$-$C_6$-haloalkoxy, $C_3$-$C_8$-cycloalkoxy, or $C_3$-$C_8$-halocycloalkoxy;

$R^9$ H;

$C_1$-$C_6$-alkyl, $C_2$-$C_6$-alkenyl, $C_2$-$C_6$-alkynyl, which are unsubstituted, or substituted by $R^{91}$;

$C_3$-$C_6$-cycloalkyl, $C_3$-$C_6$-halocycloalkyl, which are unsubstituted, or substituted by $R^{92}$ $N(R^{93})R^{94}$;

phenyl, heterocyclyl, or hetaryl which are unsubstituted, or substituted by $R^D$; or $C_1$-$C_6$-alkyl-C(=O), $C_1$-$C_6$-haloalkyl-C(=O), $C_1$-$C_6$-alkyl-OC(=O), $C_1$-$C_6$-alkenyl-OC(=O), or $C_6$-$C_{12}$-aryl-$C_1$-$C_6$-alkyl-OC(=O);

$R^{91}$ halogen, OH, CN, $C_1$-$C_4$-alkoxy, $C_1$-$C_4$-haloalkoxy, $C_1$-$C_4$-alkyl-$S(O)_m$, $C_1$-$C_4$-haloalkyl-$S(O)_m$, C(=O)N($R^A$)$R^B$;

$C_3$-$C_6$-cycloalkyl, $C_3$-$C_6$-halocycloalkyl, which are unsubstituted, or substituted by $R^C$;

phenyl, heterocyclyl, or hetaryl which rings are unsubstituted, or substituted by $R^D$;

$R^A$, $R^{93}$ H, $C_1$-$C_3$-alkyl, or $C_1$-$C_3$-haloalkyl;

$R^B$ H, $C_1$-$C_3$-alkyl, $C_1$-$C_3$-haloalkyl, $C_2$-$C_3$-alkenyl, $C_2$-$C_3$-haloalkenyl, $C_2$-$C_3$-alkynyl, $C_2$-$C_3$-haloalkynyl, $C_1$-$C_3$-alkoxy, $C_1$-$C_3$-haloalkoxy, $C_3$-$C_4$-halocycloalkyl; or $C_3$-$C_4$-cycloalkyl, $C_3$-$C_4$-halocycloalkyl, $C_3$-$C_4$-cycloalkylmethyl, $C_3$-$C_4$-halocycloalkylmethyl, wherein the cyclic groups are unsubstituted, or substituted by CN;

$R^C$ OH, CN, $C_1$-$C_2$-alkyl, or $C_1$-$C_2$-haloalkyl;

$R^D$ halogen, CN, $NO_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_4$-cycloalkylmethyl, or $C_3$-$C_4$-halocycloalkylmethyl; or two $R^D$ present on the same carbon atom of a saturated, or partially saturated ring form together a carbonyl group (=O);

$R^{92}$ $C_1$-$C_2$-alkyl, $C_1$-$C_2$-haloalkyl, or a group as defined for $R^{91}$;

$R^{94}$ C(=O)N($R^A$)$R^B$, C(=O)$OR^A$; or phenyl, heterocyclyl, or hetaryl which rings are unsubstituted, or substituted by $R^D$;

$R^{10}$ H, CN, methyl, or halomethyl;

$R^{11}$ H, $C_1$-$C_6$-alkyl-C(=O), $C_1$-$C_6$-haloalkyl-C(=O), $C_1$-$C_6$-alkyl-OC(=O), $C_1$-$C_6$-alkenyl-OC(=O), or $C_6$-$C_{12}$-aryl-$C_1$-$C_6$-alkyl-OC(=O);

$R^{12}$ H, $C_1$-$C_6$-alkyl, $C_2$-$C_6$-alkenyl, $C_2$-$C_6$-alkynyl, which are unsubstituted, or substituted by $R^{91}$;

$C_3$-$C_6$-cycloalkyl, $C_3$-$C_6$-halocycloalkyl, which are unsubstituted, or substituted by $R^{92}$; or phenyl, heterocycyl, or hetaryl which rings are unsubstituted, or substituted by $R^D$;

n is 0, or 1;

m is 0, 1, or 2;

and the N-oxides, stereoisomers and agriculturally or veterinarily acceptable salts thereof.

The invention also relates to a process for the preparation of compounds of formula I, by reaction of compounds of formula II

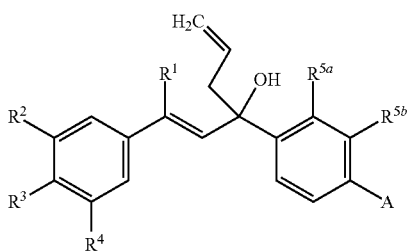

with a base at a temperature from −100 to 0° C., followed by rearrangement at a temperature from −50 to 150° C.; wherein all substituents have a meaning as defined for compounds of formula I. The invention also relates to the use of compounds of formula II for the preparation of compounds of formula I.

The invention also relates to compounds of formula II; and to compounds of formula III, which may be produced from compounds of formula I,

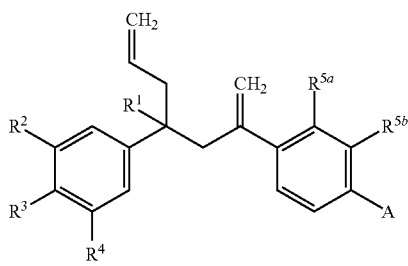

wherein all substituents have a meaning as defined for compounds of formula I.

The invention also relates to a process for the preparation of compounds of formula IV, wherein compounds of formula III

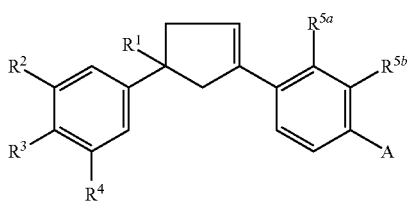

are reacted in the presence of an alkylidene-metal catalyst; wherein all substituents have a meaning as defined for compounds of formula I.

The invention also relates to the use of compounds of formula I for the preparation of compounds of formula IV.

Combinations of embodiments are within the scope of the invention.

Compounds of formulae I, II, and III are novel. They are valuable intermediates for the preparation of active ingredients IV.

Compounds of formula IV have a quaternary carbon atom in the cyclopentene ring. Quaternary carbons in cyclic systems are challenging for industrial production.

The preparation of compounds of formula IV has been described in WO2015/114157. The processes described therein have several disadvantages, interalia low yields, many reaction steps, lots of side products, and the use of triflate derivatives (cf. Schemes 3, 6, 8; and Synthesis Examples S.1 and S.3). Triflates are expensive to produce and corrosive towards production plants. Triflates also hold a poor atom economy in chemical reactions, which translates to an increased amount of waste and a low environmental sustainability.

The present invention avoids these disadvantages by a pericyclic Oxy-Cope rearrangement. Oxy-Cope reactions for the preparation of quaternary carbon atoms have been described by Jung et al., J. Am. Chem. Soc., 2005, 127(32), pp 11206-11207 and Pohmakotr et al., Chem. Ber., 1979, 112, pp. 1420-1439. It has now been found that compounds of formula I can advantageously be produced in high yields, and few reaction steps, by an Oxy-Cope rearrangement from the electron-poor compounds of formula II. The process is suitable for industrial-scale production, has a good atom economy, high selectivity, little side-products, low waste, cheap educts, and avoids all other mentioned disadvantages of prior art.

Compounds of formula I are produced by reaction of compounds of formula II

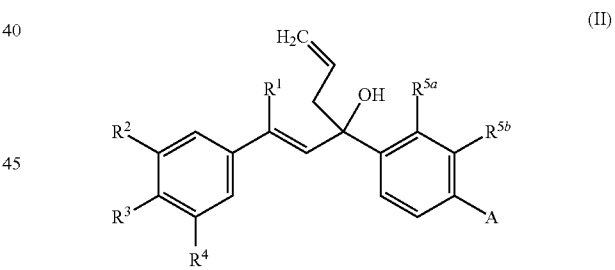

with a base at a temperature from −100 to 50° C., followed by rearrangement at a temperature from −50 to 150° C.; wherein all substituents have a meaning as defined for compounds of formula I.

In one embodiment, the temperature for the reaction of the base with compounds of formula II is −90 to 0° C. In another embodiment, the temperature for the reaction of the base with compounds of formula I is −90 to −20° C. In another embodiment, the temperature for the reaction of the base with compounds of formula II is −85 to −50° C. In another embodiment, the temperature for the reaction of the base with compounds of formula II is −85 to −65° C.

Usually, a crown ether is added for the reaction of compounds of formula II with a base. Suitable crown ethers are 12-crown-4, 18-crown-6, dibenzo-18-crown-6, or diaza-18-crown-6. In one embodiment, the crown ether is 18-crown-6. Typically, a crown ether is added if the base contains an alkali metal cation, such as a sodium or potassium cation, especially a potassium cation.

In one embodiment, the temperature for the rearrangement is −20 to 150° C. In another embodiment, the temperature for the rearrangement is 0 to 100° C. In another embodiment, the temperature for the rearrangement is 10 to 50° C. In another embodiment, the temperature for the rearrangement is 20 to 40° C. In another embodiment, the temperature for the rearrangement is −20 to 50° C. In another embodiment, the temperature is −10 to 40° C.

The reaction is usually carried out in a solvent. Suitable solvents for the reaction are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, preferably $C_1$-$C_6$-cycloalkyl ethers, $C_1$-$C_6$-alkyl-$C_1$-$C_6$-alkyl ethers and $C_1$-$C_6$-alkyl-$C_6$-$C_{10}$-aryl ethers, such as $CH_3CH_2OCH_2CH_3$, $(CH_3)_2CHOCH(CH_3)_2$, $CH_3OC(CH_3)_3$ (MTBE), $CH_3OCH_3$ (DME), tetrahydrofuran (THF), dioxane, and anisole; esters, preferably esters of aliphatic $C_1$-$C_6$-alcohols with aliphatic $C_1$-$C_6$-carboxylic acids, esters of aromatic $C_6$-$C_{10}$-alcohols with aromatic $C_6$-$C_{10}$-carboxylic acids, cyclic esters of w-hydroxy-$C_1$-$C_6$-carboxylic acids, such as $CH_3C(O)OCH_2CH_3$, $CH_3C(O)OCH_3$, $CH_3C(O)OCH_2CH_2CH_3$, $CH_3C(O)OCH(CH_3)CH_2CH_3$, $CH_3C(O)OC(CH_3)_3$, $CH_3CH_2CH_2C(O)OCH_2CH_3$, $CH_3CH(OH)C(O)OCH_2CH_3$, $CH_3CH(OH)C(O)OCH_3$, $CH_3C(O)OCH_2CH(CH_3)_2$, $CH_3C(O)OCH(CH_3)_2$, $CH_3CH_2C(O)OCH_3$, benzyl benzoate, and γ-butyrolactone; carbonates, such as ethylene carbonate, propylene carbonate, $CH_3CH_2OC(O)OCH_2CH_3$, and $CH_3OC(O)OCH_3$; nitriles, preferably $C_1$-$C_6$-nitriles, such as $CH_3CN$, and $CH_3CH_2CN$; ketones, preferably $C_1$-$C_6$-alkyl-$C_1$-$C_6$-alkyl ketones, such as $CH_3C(O)CH_3$, $CH_3C(O)CH_2CH_3$, $CH_3CH_2C(O)CH_2CH_3$, and $CH_3C(O)C(CH_3)_3$ (MTBK); alcohols, preferably $C_1$-$C_4$-alcohols, such as $CH_3OH$, $CH_3CH_2OH$, $CH_3CH_2CH_2OH$, $CH_3CH(OH)CH_3$, $CH_3(CH_2)_3OH$, and $C(CH_3)_3OH$; amides and urea derivatives, preferably dimethylformamide (DMF), N-methyl-2-pyrrolidone (NMP), dimethylacetamide (DMA), 1,3-dimethyl-2-imidazolidinone (DMI), 1,3-dimethyl-3,4,5,6-tetrahydro-2(1H)-pyrimidinone (DMPU), hexamethylphosphamide (HMPA); sulfoxides, or sulfonyles, preferably dimethyl sulfoxide (DMSO), sulfolane; and water.

Usually, the solvent is an aliphatic, or aromatic hydrocarbon, a halogenated hydrocarbon, or an ether. In another embodiment, the solvent is an aliphatic, or aromatic hydrocarbon, or an ether. In another embodiment, the solvent is an aromatic hydrocarbon, or an ether. In another embodiment, the solvent is an aliphatic, or aromatic hydrocarbon. In another embodiment, the solvent is an aliphatic $C_5$-$C_{16}$-hydrocarbon, $C_6$-$C_{10}$-aromatic hydrocarbon, halogenated aliphatic $C_1$-$C_6$-alkane, halogenated aromatic $C_6$-$C_{10}$-hydrocarbon, $C_1$-$C_6$-cycloalkyl ether, $C_1$-$C_6$-alkyl-$C_1$-$C_6$-alkyl ether, or $C_1$-$C_6$-alkyl-$C_6$-$C_{10}$-aryl ethers. In another embodiment, the solvent is an aliphatic $C_5$-$C_{16}$-hydrocarbon, a $C_6$-$C_{10}$-aromatic hydrocarbon, a $C_1$-$C_6$-cycloalkyl ether, a $C_1$-$C_6$-alkyl-$C_1$-$C_6$-alkyl ether, or a $C_1$-$C_6$-alkyl-$C_6$-$C_{10}$-aryl ether. In another embodiment, the solvent is an aliphatic $C_5$-$C_{16}$-hydrocarbon, an aromatic $C_6$-$C_{10}$-hydrocarbon, or a $C_1$-$C_6$-cycloalkyl ether. In another embodiment, the solvent is an aromatic $C_6$-$C_{10}$-hydrocarbon, or a $C_1$-$C_6$-cycloalkyl ether. In another embodiment, the solvent is an aliphatic $C_5$-$C_{16}$-hydrocarbon, or $C_6$-$C_{10}$-aromatic hydrocarbon. In another embodiment, the solvent is an aromatic $C_6$-$C_{10}$-hydrocarbon. In another embodiment, the solvent is an aliphatic $C_5$-$C_{16}$-hydrocarbon. In another embodiment, the solvent is a halogenated aliphatic $C_1$-$C_6$-alkane. In another embodiment, the solvent is a halogenated aromatic $C_6$-$C_{10}$ hydrocarbon. In another embodiment, the solvent is a $C_5$-$C_{16}$-alkane. In another embodiment, the solvent is a $C_1$-$C_6$-cycloalkyl ether, a $C_1$-$C_6$-alkyl-$C_1$-$C_6$-alkyl ether, or a $C_1$-$C_6$-alkyl-$C_6$-$C_{10}$-aryl ether. In another embodiment, the solvent is a $C_1$-$C_6$-cycloalkyl ether. In another embodiment, the solvent is benzene, toluene, or xylene. In another embodiment, the solvent is toluene, or xylene. In another embodiment, the solvent is toluene. In another embodiment, the solvent is benzene. In another embodiment, the solvent is xylene. In another embodiment, the solvent is an ether, preferably THF or dioxane. Usually, the solvent is THF, toluene, or xylene. In another embodiment, the solvent is benzene, toluene, xylene, THF, or dioxane. In another embodiment, the solvent is toluene, xylene, THF, or dioxane. It is also possible to use mixtures of the solvents mentioned. In particular, the solvent may be a mixture of a aromatic hydrocarbons and ethers, such as a mixture of toluene, xylene, dioxane and/or THF.

The melting point of the solvent is usually below 0° C., preferably below −50° C., most preferably below −80° C. Usually, the solvent is a non-polar solvent. The polarity of the solvent can be characterized by its dipole moment. In one embodiment, the solvent has a dipole moment from 0 D to 3 D, preferably from 0 D to 2 D, and most preferably from 0 D to 1.5 D (wherein D means the unit Debye).

Suitable bases are, in general, inorganic bases, such as alkali metal and alkaline earth metal hydroxides, such as LiOH, NaOH, KOH, and $Ca(OH)_2$; alkali metal and alkaline earth metal oxides, such as $Li_2O$, $Na_2O$, CaO, and MgO; alkali metal and alkaline earth metal hydrides, such as LiH, NaH, KH and $CaH_2$; alkali metal and alkaline earth metal carbonates, such as $Li_2CO_3$, $K_2CO_3$ and $CaCO_3$; alkali metal bicarbonates, such as $NaHCO_3$; organic bases, for example secondary amines, such as pyrrolidine; tertiary amines, such as diisopropylethylamine, trimethylamine, triethylamine, triisopropylamine and N-methylpiperidine, imidazole, pyridine; substituted pyridines, such as collidine, lutidine and 4-dimethylaminopyridine, and polycyclic amides and amidines, such as 1,8-diazabicycloundec-7-ene (DBU), 1,4-Diazabicyclo[2.2.2]octane (DABCO); alkali metal salts of secondary amines, such as alkali diisopropylamide, alkali bis(trimethylsilyl)amide, alkali tetramethylpiperidine; alcoholates, such as alkali methanolate, alkali ethanolate, alkali isopropanolate, alkali tert-butanolate; alkali metal—alkyl, and alkali metal—aryl salts, such as n-butyl lithium, tert-butyl lithium, phenyl lithium. The base is typically a potassium salt. The $pK_b$-value of the base may be up to 0, preferably up to −3, most preferably up to −5. The $pK_b$-value of the base may be from −25 to 0, preferably from −15 to 0, more preferably from −12 to 0. Usually, the base is an alkali alcoholate, preferably a potassium salt of an alcoholate, such as potassium tert-butanolate, or an alkali salt of a secondary amine, preferably a potassium salt of a secondary amine, such as potassium bis(trimethylsilyl)amide (KHMDS). In another embodiment, the base is an alkali alcoholate, preferably a potassium salt of an alcoholate, such as potassium tert-butanolate, an alkali salt of a secondary amine, preferably a potassium salt of a secondary amine, such as potassium bis(trimethylsilyl)amide (KHMDS), or an alkali metal or alkaline earth metal hydrides, such as NaH or KH, preferably KH. In one embodiment, the base is an alkali alcoholate. In another embodiment, the base is an alkali metal salt of a secondary amine. In another embodiment, the base is an alkali metal or alkaline earth metal hydride. In another embodiment, the base is alkali diisopropylamide, or alkali bis(trimethylsilyl)amide, such as lithium diisopropylamide, lithium bis(trimethylsilyl)amide, sodium bis(trimethylsilyl)amide, or potassium bis(trimethylsilyl)-amide. In another embodiment, the base is an alkali bis(trimethylsilyl) amide, such as lithium bis(trimethylsilyl)amide, sodium bis(trimethylsilyl)amide, or potassium bis(trimethylsilyl)-amide, in particular potassium bis(trimethylsilyl)amide. In another embodiment, the base is an alcoholate, in particular an alkali alcoholate, such as sodium alcoholate or a potassium alcoholate, especially an alkali tert-butanolate, such as potassium tert-butanolate. In another embodiment, the base is an alkali metal or alkaline earth metal hydride, such as NaH. In another embodiment, the base is not an alkali metal or alkaline earth metal hydride, such as NaH or KH, especially not NaH; and in particular not NaH if the crown ether is 18-crown-6. In another embodiment, the base is an alkali metal-alkyl, or alkali metal-aryl salt, such as n-butyl lithium, tert-butyl lithium, or phenyl lithium. In another embodiment, the base is an alcoholate, or an alkali metal salt of a secondary amine, such as alkali methanolate, alkali ethanolate, alkali isopropanolate, alkali diisopropylamide, or alkali bis(trimethylsilyl)amide. Mixtures of the aforementioned bases are also possible. The bases are generally employed in catalytic amounts; however, they can also be used in equimolar amounts, in excess or, if appropriate, as solvent. Usually, the reaction of compounds of formula II with a base, and subsequent rearrangement is carried out in a one-pot synthesis.

Compounds of Formula I May be Reacted with an Olefinating Agent to Compounds of Formula III

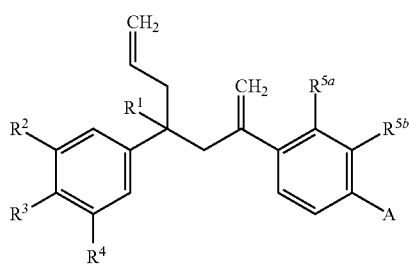

(III)

wherein all substituents have a meaning as defined for compounds of formula I.

The reaction is usually carried out at temperatures from −100 to 150° C., preferably from 0 to 50° C., and most preferably from 10 to 40° C. in a solvent.

Suitable solvents are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, preferably $C_1$-$C_6$-cycloalkyl ethers, $C_1$-$C_6$-alkyl-$C_1$-$C_6$-alkyl ethers and $C_1$-$C_6$-alkyl-$C_6$-$C_{10}$-aryl ethers, such as $CH_3CH_2OCH_2CH_3$, $(CH_3)_2CHOCH(CH_3)_2$, MTBE, DME, $CH_3OCH_2CH_2OCH_3$, dioxane, anisole, and tetrahydrofuran (THF); nitriles, preferably $C_1$-$C_6$-nitriles, such as $CH_3CN$, and $CH_3CH_2CN$; alcohols, preferably $C_1$-$C_4$-alcohols, such as $CH_3OH$, $CH_3CH_2OH$, $CH_3CH_2CH_2OH$, $CH_3CH(OH)CH_3$, $CH_3(CH_2)_3OH$, and $C(CH_3)_3OH$. In one embodiment, the solvent is an ether, preferably a $C_1$-$C_6$-cycloalkyl ether, such as THF. In another embodiment, the solvent is an aromatic $C_6$-$C_{10}$-hydrocarbon, such as benzene, toluene, o-, m-, and p-xylene, preferably toluene. Mixtures of the aforementioned solvents are also possible.

Suitable olefinating agents are usually selected from methyl phosphonium ylides, Tebbe's reagent bis(cyclopentadienyl)-μ-chloro(dimethylaluminum)-μ-methylene-titanium, Petasis reagent (Bis($\eta^5$-cyclopentadienyl)dimethyltitanium), or Lombardo reagent. The Lombardo reagent may be produced in situ from Zn, $TiCl_4$, and $CH_2Br_2$, as described in Lombardo L., Org. Synth., 1987, vol. 65, p. 81. Tebbe's reagent is commercially available. The Petasis reagent may be produced from bis(cyclopentadienyl)titanium(IV) dichloride, which is commercially available, and methyl lithium. Methyl phosphonium ylides may be produced from phosphines with methylhalides, followed by treatment with a base, e.g. an alkali alcoholate, a alkali salt of a secondary amine, or an alkali salt of an alkyl or aryl, e.g. potassium tert-butanolate, or n-butyl lithium, as described in Davies H., Walji A., Angewandte Chemie International Edition, 2005, vol. 44, p. 1733-1735, Supplementary Information. The starting materials are generally reacted with one another in equimolar amounts. In terms of yield, it may be advantageous to employ an excess of the olefinating agent. The olefinating agent is either produced in situ, or it is produced before the addition of compounds of formula I.

In one embodiment, the olefination agent is a methyl phosphonium ylide, such as methyl triphenyl phosphonium ylide. Methyl phosphonium ylides are commercially available, or can be prepared by reaction of phosphines with methylhalides in the presence of a base, such as phenyl lithium, or n-butyl lithium.

Compounds of Formula III May be Reacted to Compounds of Formula IV in the Presence of an Alkylidene-Metal Catalyst

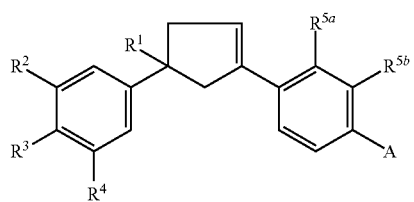

(IV)

wherein all substituents have a meaning as defined for compounds of formula I.

The reaction is usually carried out at temperatures from −100 to 150° C., preferably from 0 to 50° C., and most preferably from 10 to 40° C. in the presence of a solvent.

Suitable solvents are aliphatic hydrocarbons, preferably an aliphatic $C_5$-$C_{16}$-hydrocarbon, more preferably a $C_5$-$C_{16}$-alkane, or $C_5$-$C_{16}$-cycloalkane, such as pentane, hexane, cyclohexane, or petrol ether; aromatic hydrocarbons, preferably an aromatic $C_6$-$C_{10}$-hydrocarbons, such as benzene, toluene, o-, m-, and p-xylene; halogenated hydrocarbons, preferably halogenated aliphatic $C_1$-$C_6$-alkanes, or halogenated aromatic $C_6$-$C_{10}$-hydrocarbons, such as $CH_2Cl_2$, CHCl$_3$, CCl$_4$, CH$_2$ClCH$_2$Cl, CCl$_3$CH$_3$, CHCl$_2$CH$_2$Cl, or chlorobenzene; ethers, preferably C$_1$-C$_6$-cycloalkyl ethers, C$_1$-C$_6$-alkyl-C$_1$-C$_6$-alkyl ethers and C$_1$-C$_6$-alkyl-C$_6$-C$_{10}$-aryl ethers, such as CH$_3$CH$_2$OCH$_2$CH$_3$, (CH$_3$)$_2$CHOCH(CH$_3$)$_2$, MTBE, DME, CH$_3$OCH$_2$CH$_2$OCH$_3$, dioxane, anisole, and tetrahydrofuran (THF); and alcohols, preferably C$_1$-C$_4$-alcohols, such as CH$_3$OH, CH$_3$CH$_2$OH, CH$_3$CH$_2$CH$_2$OH, CH$_3$CH(OH)CH$_3$, CH$_3$(CH$_2$)$_3$OH, and C(CH$_3$)$_3$OH.

In one embodiment, the solvent is a halogenated C$_1$-C$_6$-alkane, or halogenated C$_6$-C$_{10}$-aromatic hydrocarbon, preferably a halogenated C$_1$-C$_6$-alkane, such as CH$_2$Cl$_2$, or CH$_2$ClCH$_2$Cl, preferably CH$_2$Cl$_2$. In another embodiment, the solvent is a C$_5$-C$_{16}$-alkane, such as pentane, hexane, cyclohexane, and petrol ether. In another embodiment, the solvent is a C$_6$-C$_{10}$-aromatic hydrocarbon, such as benzene, toluene, o-, m-, and p-xylene.

Suitable alkylidene-metal catalysts are alkylidene compounds of transition metals, such as W, Ta, Mo, Re, and Ru. Suitably alkylidene moieties are methyliden, C$_1$-C$_6$-alkyl methyliden, and C$_6$-C$_{10}$-aryl methyliden, e.g. phenylmethyliden, and tert-butyl-methylidene. In one embodiment, the alkylidene-metal catalyst is a Ru-alkylidene compound. In one embodiment, the alkylidene-metal catalyst is a W, Ta, Mo, or Ru-alkylidene compound. In another embodiment, the alkylidene-metal catalyst is a Mo-alkylidene compound. In another embodiment, the alkylidene-metal catalyst is a Ta-alkylidene compound. In another embodiment, the alkylidene-metal catalyst is a Ru-phenylmethyliden compound. In another embodiment, the alkylidene metal catalyst is a Ta-tert-butylmethyliden compound.

Examples of alkylidene-metal catalysts are dichloro(3-methyl-2-butenylidene)bis(tricyclopentylphosphine)ruthenium(II), dichloro(3-methyl-2-butenylidene)bis(tricyclohexylphosphine)ruthenium(II), dichloro[1,3-bis(2,4,6-trimethylphenyl)-2-imidazolidinylidene](3-methyl-2-butenylidene)(tricyclohexylphosphine)ruthenium(I), bis(tricyclohexylphosphine)-benzylidine ruthenium(IV) dichloride, (1,3-bis(2,4,6-trimethylphenyl)-2-imidazolidinylidene)-dichloro(p-henylmethylene)(tricyclohexylphosphine)ruthenium, dichloro(o-isopropoxyphenyl-methylene)(tricyclohexylphosphine)ruthenium(II), (1,3-bis-(2,4,6-trimethylphenyl)-2-imidazolidinylidene)dichloro(o-isopropoxyphenylmethylene) ruthenium (Hoveyda-Grubbs 1st generation), dichloro[1,3-Bis(2-methylphenyl)-2-imidazolidinylidene]-(benzylidene)-(tricyclohexylphosphine)ruthenium(II), dichloro[1,3-bis(2-methylphenyl)-2-imidazolidinylidene](2-isopropoxyphenylmethylene)-ruthenium(II), dichloro[1,3-bis(2,4,6-trimethylphenyl)-2-imidazolidinylidene][3-(2-pyridinyl)propylidene]ruthenium(II), dichloro[1,3-bis(2,4,6-trimethylphenyl)-2-imidazolidinylidene](benzylidene)bis(3-bromopyridine)-ruthenium(II). In one embodiment, the alkylidene metal catalyst is (1,3-bis(2,4,6-trimethylphenyl)-2-imidazolidinylidene)dichloro(phenylmethylene)-(tricyclohexylphosphine)ruthenium. The catalysts are generally employed in catalytic amounts; however, they can also be used in equimolar amounts, or in excess.

Compounds of Formula II May be Produced by Reaction of Compounds of Formula V

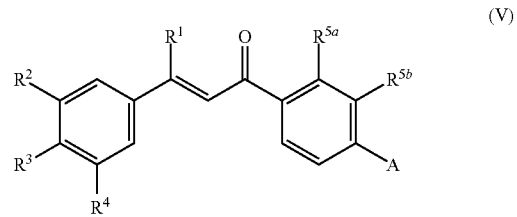

with an allylation reagent; wherein all substituents have a meaning as defined for compounds of formula I.

Additionally, a Lewis acid may be added to the reaction mixture, preferably a Ti, B or Zn containing compound, such as boron halide, dimethyltitaniumdihalide, or titanocene dihalide, especially BF$_3$, or dimethyl titanium dichloride, or titanocene dichloride. In one embodiment, the Lewis acid may be a metallocene compound, preferably a Ti-(IV) metallocene, and in particular titanocene dihalide, such as titanocene dichloride.

The reaction is usually carried out at a temperature from −100 to 100° C., preferably −78 to 50° C., in particular −20 to 40° C. in an inert solvent.

Suitable solvents are aliphatic hydrocarbons, preferably an aliphatic C$_5$-C$_{16}$-hydrocarbon, more preferably a C$_5$-C$_{16}$-alkane, or C$_5$-C$_{16}$-cycloalkane, such as pentane, hexane, cyclohexane, or petrol ether; aromatic hydrocarbons, preferably an aromatic C$_6$-C$_{10}$-hydrocarbons, such as benzene, toluene, o-, m-, and p-xylene; halogenated hydrocarbons, preferably halogenated aliphatic C$_1$-C$_6$-alkanes, or halogenated aromatic C$_6$-C$_{10}$-hydrocarbons, such as CH$_2$Cl$_2$, CHCl$_3$, CCl$_4$, CH$_2$ClCH$_2$Cl, CCl$_3$CH$_3$, CHCl$_2$CH$_2$Cl, CCl$_2$CCl$_2$, or chlorobenzene; ethers, preferably C$_1$-C$_6$-cycloalkyl ethers, C$_1$-C$_6$-alkyl-C$_1$-C$_6$-alkyl ethers and C$_1$-C$_6$-alkyl-C$_6$-C$_{10}$-aryl ethers, such as CH$_3$CH$_2$OCH$_2$CH$_3$, (CH$_3$)$_2$CHOCH(CH$_3$)$_2$, MTBE, DME, CH$_3$OCH$_2$CH$_2$OCH$_3$, dioxane, anisole, and tetrahydrofuran (THF); alcohols, preferably C$_1$-C$_4$-alcohols, such as CH$_3$OH, CH$_3$CH$_2$OH, CH$_3$CH$_2$CH$_2$OH, CH$_3$CH(OH)CH$_3$, CH$_3$(CH$_2$)$_3$OH, and C(CH$_3$)$_3$OH; amides and urea derivatives, preferably DMF, NMP, DMA, DMI, and DMPU.

Usually, the solvent is an ether, or DMF. In another embodiment, the solvent is an ether, preferably THF, or CH$_3$CH$_2$OCH$_2$CH$_3$, in particular when A is halogen, C$_1$-C$_6$-alkoxy, C$_6$-C$_{10}$-aryloxy, C$_1$-C$_6$-haloalkoxy, C$_6$-C$_{10}$-arylalkoxy, or C$_6$-C$_{10}$-aryl-C$_1$-C$_6$-alkoxy. In another embodiment, the solvent is DMF, in particular when A is CN, OS(O)$_2$R$^6$, A$^1$, or A$^2$. In another embodiment, the solvent is a halogenated hydrocarbon, e.g. CH$_2$Cl$_2$, in particular when A is CN, OS(O)$_2$R$^6$, A$^1$, or A$^2$.

Allylation reagents are usually a) allyl-metal compounds; b) compositions of metals with allyl-halides or allyl-acetate; c) allyl-silanes, and derivatives thereof; d) allyl-boranes, and derivatives thereof.

The metal within the a) allyl-metal compound is usually Mg, Li, Zn, In, Ga, Ti, Sm, Cu, Cd, Al, Sn, or Ce. In one embodiment, the metal within the allyl-metal compound is Mg, Li, In, Zn, Ti, Cu, Al, or Ce. In another embodiment, the metal within the allyl-metal compound is Mg, Li, Zn, In, Ti, or Ce. In another embodiment, the metal within the allyl-metal compound is Mg, or Li. In another embodiment, the metal within the allyl-metal compound is Zn, In, Ti, or Ce. In another embodiment, the metal within the allyl-metal compound is Zn, or In. In another embodiment, the metal within the allyl-metal compound is Mg, Li, In, or Zn. In another embodiment, the metal within the allyl-metal compound is Mg, In, or Zn. In another embodiment, the metal within the allyl-metal compound is Mg, or Zn.

In case A is CN, OS(O)$_2$R$^6$, A$^1$, or A$^2$, the metal within the a) allyl-metal compound is usually Zn, In, or Ce, preferably Zn or In, more preferably Zn. In case A is halogen, C$_1$-C$_6$-alkoxy, C$_6$-C$_{10}$-aryloxy, C$_1$-C$_6$-haloalkoxy, C$_6$-C$_{10}$-arylalkoxy, C$_6$-C$_{10}$-aryl-C$_1$-C$_6$-alkoxy, the metal within the allyl-metal compound is usually Mg, or Li, preferably Mg.

Suitably allyl-metal compounds are monoallyl-metal compounds, such as allyllithium; monoallyl-metal halides, such as allylmagnesium halide, e.g. allylmagnesium chloride, or allylmagnesium bromide, allylzinc halides, e.g. as allylzinc chloride, or allylzinc bromide, allylindium dihalides, e.g. allylindium dichloride, allylindium dibromide, or allylindium diiodide, allyl cerium dihalide, e.g. allyl cerium dichloride, or allyl cerium dibromide, allylcopper halides, e.g. allylcopper chloride, or allylcopper bromide, allyltitanium trihalide, e.g. allyltitanium trichloride, or allyl titanium tribromide; diallyl-metal compounds, such as diallyl zinc, or diallyl copper; diallyl-metal halides, such as diallylindium halides, e.g. diallylindium chloride, diallylindium bromide, or diallylindium iodide, diallyl cerium halide, e.g. diallyl cerium chloride, or diallyl cerium bromide, diallyl-titanium dihalide, e.g. diallyl titanium dichloride, or diallyl titanium dibromide, diallylaluminium halides, e.g. diallylaluminium chloride, or diallylaluminium bromide; triallyl-metal compounds, such as triallyl cerium, or tiallylaluminium; triallyl-metal halides, such as triallyltitanium halide, e.g. triallyltitanium chloride, or triallyltitanium bromide; or tetrallyl-metal compounds, such as tetraallyltitanium; in particular monoallyl-metal compounds, monoallyl-metalhalides, diallyl-metal compounds, and diallyl-metal halides, e.g. allyllithium, allylmagnesium halide, allylzinc halide, diallylzinc, monoallyl cerium dihalide, diallyl cerium halide, triallyl cerium, or triallylaluminium. In one embodiment, the allyl metal compound is allyllithium, allylmagnesium halide, allylindium dihalide, allylzinc halide, or diallylzinc. In another embodiment, the allyl metal compound is allyllithium, or allylmagnesium halide. In another embodiment, the allyl metal compound is allylzinc halide, diallylzinc, or allylindium dihalide. In another embodiment, the allyl metal compound is allylzinc halide, or diallylzinc.

In case A is CN, OS(O)$_2$R$^6$, A$^1$, or A$^2$, the ally-metal compound is usually allylzinc halide, diallylzinc, allylindium dihalide, or allyl cerium dihalide, preferably allylzinc halide, diallylzinc, or allylindium dihalide, more preferably allylzinc halide, or diallylzinc, and in particular allylzinc halide. In case A is halogen, C$_1$-C$_6$-alkoxy, C$_6$-C$_{10}$-aryloxy, C$_1$-C$_6$-haloalkoxy, C$_6$-C$_{10}$-arylalkoxy, or C$_6$-C$_{10}$-aryl-C$_1$-C$_6$-alkoxy, the ally-metal compound is usually allyllithium, or allylmagnesium halide.

Suitable allyl-halides are allyl-chloride, allyl-bromide, or allyl-iodide. In one embodiment, the allyl-halide is allyl-chloride. In one embodiment, the allyl-halide is allyl-bromide. In one embodiment, the allyl-halide is allyl-iodide.

The metal in b) compositions of metals with allyl-halides, or allyl-acetates is usually a metal of groups 1, 2, 13, or a transition metal of groups 6, 7, 8, 9, 10, or 12. Typical metals for use in an allylation reagent are Mg, Mn, Li, Zn, In, Ir, Ga, Ti, Sm, Pd, Pt, Cu, Cd, Al, Sn, or Ce. In one embodiment, the metal is Mg, Li, Zn, In, Pd, Ir, Ti, Al, or Ce. In another embodiment, the metal is Mg, Li, Zn, In, Pd, or Ce. In yet another embodiment, the metal is Mg, Li, In, or Zn. In yet another embodiment, the metal is Mg, Li, or Zn. In yet another embodiment, the metal is Mg, Li, Mn, In, or Zn. In yet another embodiment, the metal is Mg, or Li. In yet another embodiment, the metal is Zn, or Li. In yet another embodiment, the metal is Mg. In yet another embodiment, the metal is Li. In yet another embodiment, the metal is Zn. In yet another embodiment, the metal is Ce. In yet another embodiment, the metal is Mn. In yet another embodiment, the metal is Mn. In yet another embodiment, the metal is Pd. In case the allylation reagent is b) a composition of metals with allyl-acetate, the metal is usually Pt, Pd, or Ir, preferably Pd or Ir, most preferably Pd.

In case A is CN, OS(O)$_2$R$^6$, A$^1$, or A$^2$, the metal in b) compositions of metals with allyl-halides, or allyl-acetates is usually Zn, Pd, Ir, or In, preferably In, or Zn, most preferably Zn. In case A is halogen, C$_1$-C$_6$-alkoxy, C$_6$-C$_{10}$-aryloxy, C$_1$-C$_6$-haloalkoxy, C$_6$-C$_{10}$-arylalkoxy, C$_6$-C$_{10}$-aryl-C$_1$-C$_6$-alkoxy, the metal is usually Mg, or Li, preferably Mg.

The term c) allyl-silanes, and derivatives thereof, includes allyl-trialkyl-silanes, allyl-trialkoxy-silanes, and allyl-triphenyl-silanes, preferably allyl-trimethyl-silane The term d) allyl-boranes, and derivatives thereof, includes allyl-bornonates and their esters, and allyl-dialkyl-boranes.

The starting materials are generally reacted with one another in equimolar amounts. In terms of yield, it may be advantageous to employ an excess of the allyl-halide and the metal, or the allyl-metal compound, with regard to compounds of formula V. Compounds of formula V may be produced by an aldol-condensation as described in WO2015/128358 (p. 92, Scheme 3 and p. 145, Synthesis Example S.1) or EP2172462 (paragraphs 0020, Synthesis Examples).

The production of compounds of formula I from compounds of formula V may also be carried out as a one-pot-synthesis, i.e. without intermediate isolation of compounds of formula II. Hence, the invention also relates to a method for production of compounds of formula I from compounds of formula V, wherein compounds of formula V are converted to compounds of formula II by addition of an allyl-halide and a metal, or an allyl-metal compound, and wherein subsequently compounds of formula II are converted to compounds of formula I by reaction with a base at a temperature from −100 to 0° C., followed by rearrangement at a temperature from −50 to 150° C.

The reaction mixtures for the described processes are worked up in a customary manner, for example by mixing with water, separating the phases and, if appropriate, chromatographic purification of the crude products. Some of the intermediates and end products are obtained in the form of colorless or slightly brownish viscous oils, which are purified, or freed from volatile components under reduced pressure and at moderately elevated temperature. If the intermediates and end products are obtained as solids, purification can also be carried out by recrystallization, or digestion.

If individual compounds of formula I, II, III, IV, or V cannot be obtained by the routes described above, they can be produced by derivatization of other compounds of formula I, II, III, IV, or V.

The terms for organic groups used in the definition of the variables and solvents, such as, for example, the term "halogen", are collective terms, which represent the individual members of these groups of organic moieties. In each case, the prefix C$_x$-C$_y$ denotes the number of possible carbon atoms.

The term "halogen" refers in each case to fluorine, chlorine, bromine or iodine. In another embodiment, the term halogen refers to chlorine, bromine, or iodine. In yet another embodiment, the term halogen refers to bromine, or iodine. In yet another embodiment, the term halogen refers to bromine.

In all above cases $C_5$-$C_{16}$ alkanes means n-pentane, n-hexane, n-heptane, n-octane, n-nonane, n-decane, n-undecane, n-dodecane, n-tridecane, n-tetradecane, n-hexadecane, isopentane, neopentane, 2-methyl pentane, 3-methyl pentane, 2,2-dimethylpentane, as well as all isomers of heptane, octane, nonane, decane, undecane, dodecane, tridecan, and the mixture of the aforementioned $C_5$-$C_{12}$ alkanes. The term "alkyl", as used in $C_1$-$C_6$-alkyl, $C_1$-$C_4$-alkyl and in the terms $C_1$-$C_6$-alkoxy, refers to a saturated straight-chain or branched hydrocarbon group, for example methyl, ethyl, propyl, 1-methylethyl, butyl, 1-methylpropyl, 2-methylpropyl, 1,1-dimethylethyl, pentyl, 1-methylbutyl, 2-ethylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

The term "$C_2$-$C_6$-alkenyl" refers to monounsaturated straight-chain or branched hydrocarbon radicals having 2 to 6 carbon atoms, and a C=C double bond in any position, such as ethenyl, 1-propenyl, 2-propenyl, 1-methylethenyl, 1-butenyl, 2-butenyl, 3-.

The term "$C_2$-$C_6$-alkynyl" refers to monounsaturated straight-chain or branched hydrocarbon radicals having 2 to 6 carbon atoms, and a C≡C triple bond in any position, for example $C_2$-$C_6$-alkynyl, such as ethynyl, 1-propynyl, and 2-propynyl.

The term "$C_1$-$C_6$-alkoxy" refers to straight-chain or branched saturated alkyl groups comprising 1 to 6 carbon atoms, which groups are attached via an oxygen atom. Examples include $C_1$-$C_6$-alkoxy, such as, for example, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$ and $OC(CH_3)_3$.

The term "$C_1$-$C_6$-haloalkyl", as used herein and in the haloalkyl moieties of $C_1$-$C_6$-haloalkoxy and $C_1$-$C_6$-haloalkylthio, refers to straight-chain or branched alkyl groups having 1 to 6 carbon atoms, wherein some or all of the hydrogen atoms of these groups are replaced by halogen atoms, such as chloromethyl, bromomethyl, dichloromethyl, trichloromethyl, fluoromethyl, difluoromethyl, trifluoromethyl, 1-chloroethyl, 1-bromoethyl, 1-fluoroethyl, 2-fluoroethyl, 2,2-difluoroethyl, 2,2,2-trifluoroethyl, 2,2,2-trichloroethyl, pentafluoroethyl, heptafluoroisopropyl, etc.

The term "$C_2$-$C_6$-haloalkenyl" as used herein, which is also expressed as "$C_1$-$C_6$-alkenyl which is partially or fully halogenated", and the haloalkenyl moieties in haloalkenyloxy, haloalkenylcarbonyl and the like refers to unsaturated straight-chain or branched hydrocarbon radicals 2 to 6 carbon atoms and a double bond in any position (as mentioned above), wherein some or all of the hydrogen atoms in these groups are replaced by halogen atoms as mentioned above, in particular fluorine, chlorine and bromine, for example chlorovinyl, chloroallyl and the like.

The term "$C_2$-$C_6$-haloalkynyl" as used herein, which is also expressed as "$C_1$-$C_6$-alkynyl which is partially or fully halogenated", and the haloalkynyl moieties in haloalkynyloxy, haloalkynylcarbonyl and the like refers to unsaturated straight-chain or branched hydrocarbon radicals having 2 to 6 ("$C_2$-$C_6$-haloalkynyl") carbon atoms and one or two triple bonds in any position (as mentioned above), wherein some or all of the hydrogen atoms in these groups are replaced by halogen atoms as mentioned above, in particular fluorine, chlorine and bromine. The term "$C_1$-$C_6$-haloalkoxy" refers to $C_1$-$C_6$-haloalkyl groups, as defined above, which are attached via an oxygen atom. Examples include mono-, di- and trifluoromethoxy, mono-, di- and trichloromethoxy, 2,2,2-trifluoroethoxy, or heptafluoroisopropoxy.

The term "$C_3$-$C_8$-cycloalkyl", as used herein, describes cyclic hydrocarbon radicals comprising 3 to 8 carbon atoms. Examples of cyclic radicals are cyclopropyl, cyclobutyl, cyclopentyl, cyclohexyl or cycloheptyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") carbon ring members (as mentioned above) in which some or all of the hydrogen atoms are replaced by halogen atoms as mentioned above, in particular fluorine, chlorine and bromine.

The term "heterocycle" or "heterocyclyl" includes in general 3- to 12-membered, preferably 5- or 6-membered, in particular 6-membered monocyclic heterocyclic non-aromatic radicals. The heterocyclic non-aromatic radicals usually comprise 1, 2 or 3 heteroatoms selected from N, O or S as ring members, wherein S-atoms as ring members may be present as S, SO or $SO_2$. Examples of heterocyclic radicals comprise saturated or unsaturated, non-aromatic heterocyclic rings, such as 2- and 3-azetidinyl, 2- and 3-oxetanyl, 2- and 3-thietanyl, 2- and 3-thietanyl-S-oxide (S-oxothietanyl), 2- and 3-thietanyl-S-dioxide (S-dioxothietanyl), 2- and 3-pyrrolidinyl, isoxazolidinyl, i.e. 2-3-, and 4-isoxazolidinyl, 2- and 3-tetrahydrofuranyl, 1,3-dioxolan-2-yl, thiolan-2-yl, S-oxothiolan-2-yl, S-dioxothiolan-2-yl, 4- and 5-oxazolidinyl, 1,3-dioxan-2-yl, 1- and 3-thiopyran-2-yl, S-oxothiopyranyl, and S-dioxothiopyranyl.

The term "hetaryl" includes monocyclic 5- or 6-membered heteroaromatic radicals comprising as ring members 1, 2, or 3 heteroatoms selected from N, O and S. Examples of 5- or 6-membered heteroaromatic radicals include pyridyl, i.e. 2-, 3-, and 4-pyridyl, pyrimidinyl, i.e. 2-, 4- and 5-pyrimidinyl, pyrazinyl, pyridazinyl, i.e. 3- and 4-pyridazinyl, thienyl, i.e. 2- and 3-thienyl, furyl, i.e. 2- and 3-furyl, pyrrolyl, i.e. 1-, 2- and 3-pyrrolyl, oxazolyl, i.e. 2-, 4- and 5-oxazolyl, isoxazolyl, i.e. 3-, 4- and 5-isoxazolyl, thiazolyl, i.e. 2-, 3- and 5-thiazolyl, isothiazolyl, i.e. 3-, 4- and 5-isothiazolyl, pyrazolyl, i.e. 1-, 3-, 4- and 5-pyrazolyl, imidazolyl, i.e. 1-, 2-, 4- and 5-imidazolyl, oxadiazolyl, e.g. 2- and 5-[1,3,4]oxadiazolyl, thiadiazolyl, e.g. 1,3,4-thiadiazol-5-yl, 1,2,4-thiadiazol-3-yl, triazolyl, e.g. 1,3,4-triazol-2-yl, and 1,2,4-triazol-3-yl.

The term "substituted" relates in every case to a substitution with one, or more, same, or different substituents.

The term "aryl", "aromatic carbocycle", "aromatic hydrocarbon", or "aromatic carbocyclic ring" includes mono-, bi- or tricyclic aromatic radicals as well as alkyl-aryl, aryl-alkyl, and aryl-alkyl-aryl radicals having the indicated total number of carbon atoms, such as 6 to 14 carbon atoms, preferably 6, 10 or 14 carbon atoms; usually the terms "aryl", "aromatic carbocycle", "aromatic hydrocarbon", or "aromatic carbocyclic ring" relate to mono-, bi- or tricyclic aromatic radicals. Exemplary aryl groups include phenyl, benzyl, xylyl, naphthyl and anthracenyl. Phenyl is preferred as aryl group.

The term "aliphatic hydrocarbon" relates to non-aromatic hydrocarbons, i.e. linear, branched, and/or cyclic hydrocarbons that are saturated, or unsaturated, but do not include aromatic moieties. Examples of aliphatic hydrocarbons are aklanes, cycloalkanes, alkenes, and alkines.

If not otherwise stated, the preferred definitions of the different substituents relate to all compounds and processes where these are applicable. In particular, the following embodiments and preferred embodiments correspond to those of formula I, II, III, IV, and V, in case the substituent is present in the respective formula. The substituents as defined above may have the following meanings.

In one embodiment, $R^1$ is halomethyl. In another embodiment, $R^1$ is trihalomethyl. In another embodiment, $R^1$ is trifluormethyl.

In one embodiment, $R^2$ is halogen, halomethyl, or halomethoxy, and $R^3$ and $R^4$ are H, or as defined for $R^2$. In another embodiment, $R^2$ is F, Cl, Br, $CF_3$, or $OCF_3$, and $R^3$ and $R^4$ are H, or as defined for $R^2$. In another embodiment, $R^2$ is F. In another embodiment, $R^2$ is Cl. In yet another embodiment, $R^2$ is I. In yet another embodiment, $R^2$ is $CF_3$. In yet another embodiment, $R^2$ is $OCF_3$. In another embodiment, $R^2$ is F, and $R^3$ and $R^4$ are H, or F, Cl, Br, $CF_3$, or $OCF_3$. In another embodiment, $R^2$ is $C_1$, and $R^3$ and $R^4$ are H, or F, Cl, Br, $CF_3$, or $OCF_3$. In yet another embodiment, $R^2$ is I, and $R^3$ and $R^4$ are H, or F, Cl, Br, $CF_3$, or $OCF_3$. In yet another embodiment, $R^2$ is $CF_3$, and $R^3$ and $R^4$ are H, or F, Cl, Br, $CF_3$, or $OCF_3$. In yet another embodiment, $R^2$ is $OCF_3$, and $R^3$ and $R^4$ are H, or F, Cl, Br, $CF_3$, or $OCF_3$.

In one embodiment, $R^2$, $R^3$, and $R^4$ correspond to a line A-1 to A-31 of Table A.

| No. | $R^2$ | $R^3$ | $R^4$ |
|---|---|---|---|
| A-1 | F | H | F |
| A-2 | F | F | F |
| A-3 | F | Cl | F |
| A-4 | F | Br | F |
| A-5 | F | H | Cl |
| A-6 | F | H | Br |
| A-7 | Cl | H | Cl |
| A-8 | Cl | Cl | Cl |
| A-9 | Cl | F | Cl |
| A-10 | Cl | Br | Cl |
| A-11 | Cl | H | Br |
| A-12 | Br | H | Br |
| A-13 | Br | F | Br |
| A-14 | Br | Cl | Br |
| A-15 | $CF_3$ | H | F |
| A-16 | $CF_3$ | H | Cl |
| A-17 | $CF_3$ | H | Br |
| A-18 | $CF_3$ | H | $CF_3$ |
| A-19 | $CF_3$ | F | F |
| A-20 | $CF_3$ | Cl | Cl |
| A-21 | $CF_3$ | Br | Br |
| A-22 | $OCF_3$ | H | F |
| A-23 | $OCF_3$ | H | Cl |
| A-24 | $OCF_3$ | H | Br |
| A-25 | $OCF_3$ | H | $CF_3$ |
| A-26 | $OCF_3$ | H | H |
| A-27 | $CF_3$ | H | H |
| A-28 | Br | H | H |
| A-29 | Cl | H | H |
| A-30 | F | H | H |
| A-31 | Cl | F | H |

In one embodiment, $R^{5b}$ is halogen, methyl, or halomethyl, preferably F, Cl, Br, $CH_3$, or $CF_3$. In another embodiment, $R^{5b}$ is F. In another embodiment, $R^{5b}$ is Cl. In another embodiment, $R^{5b}$ is Br. In another embodiment, $R^{5b}$ is $CF_3$. In another embodiment, $R^{5b}$ is $CH_3$. In another embodiment, $R^{5b}$ is $OCF_3$.

Usually, $R^{5a}$ is H. In another embodiment, $R^{5a}$ and $R^{5b}$ form together with the C-atoms they are bound to a 5-, or 6-membered saturated ring containing no heteroatoms.

Usually, A is halogen, or a group $A^1$; preferably halogen, or a group $A^1$, wherein Y is $OR^7$; more preferably A is halogen, or a group $A^1$, wherein Y is $OR^7$, and $R^7$ is $C_1$-$C_6$-alkyl, $C_1$-$C_6$-haloalkyl, $C_1$-$C_6$-alkenyl, $C_1$-$C_6$-alkynyl, phenyl, or benzyl; in particular A is halogen, or a group $A^1$, wherein Y is $OR^7$, and $R^7$ is $C_1$-$C_4$-alkyl, phenyl, or benzyl; especially A is Br, or $A^1$ and Y is $OCH_3$.

In one embodiment, A is a group $A^1$, and Y is $OR^7$, or $N(H)R^9$. In another embodiment, A is a group $A^1$, and Y is $OR^7$. In another embodiment, A is a group $A^1$, and Y is $N(R^8)R^9$, preferably $NHR^9$. In another embodiment, A is a group $A^2$. In another embodiment, A is Cl, Br, I, or CN. In another embodiment, A is Cl, Br, or I. In another embodiment, A is Br. In another embodiment, $A^1$ and Y is $OCH_3$. In another embodiment, A is $OS(O)_2R^6$, wherein $R^6$ is preferably halogen, methyl, or tolyl, more preferably methyl, or tolyl.

In one embodiment, A is CN, $OS(O)_2R^6$, a group $A^1$, or a group $A^2$. In another embodiment, A is halogen, $C_1$-$C_6$-alkoxy, $C_6$-$C_{10}$-aryloxy, $C_1$-$C_6$-haloalkoxy, $C_6$-$C_{10}$-arylalkoxy, or $C_6$-$C_{10}$-aryl-$C_1$-$C_6$-alkoxy.

In one embodiment, $R^8$ is H, CN; or $C_1$-$C_{10}$-alkyl, $C_3$-$C_8$-cycloalkyl, $C_2$-$C_{10}$-alkenyl, or $C_2$-$C_{10}$-alkynyl, which are unsubstituted, or substituted by $R^{81}$. In another embodiment, $R^8$ is H, $C_1$-$C_6$-alkyl, or $C_1$-$C_6$-haloalkyl. In another embodiment, $R^8$ is $CH_3$. In another embodiment, $R^8$ is H. In another embodiment, $R^8$ is $C_1$-$C_6$-alkyl-$C(=O)$, $C_1$-$C_6$-haloalkyl-$C(=O)$, $C_1$-$C_6$-alkyl-$OC(=O)$, $C_1$-$C_6$-alkenyl-$OC(=O)$, or $C_6$-$C_{12}$-aryl-$C_1$-$C_6$-alkyl-$OC(=O)$.

In another embodiment, $R^8$ is $C_1$-$C_6$-alkyl-$OC(=O)$, $C_1$-$C_6$-alkenyl-$OC(=O)$, or $C_6$-$C_{12}$-aryl-$C_1$-$C_6$-alkyl-$OC(=O)$, in particular $(CH_3)_3$—$OC(=O)$ (Boc), 9-fluorenyl-$CH_2$—$OC(=O)$ (Fmoc), $CH_3C(=O)$, $CH_2CHCH_2$—$OC(=O)$ (Alloc), phenyl-$CH_2$—$OC(=O)$ (Cbz), and especially Boc, Fmoc, Alloc, and Cbz.

In one embodiment, $R^9$ is $C_1$-$C_6$-alkyl, $C_2$-$C_6$-alkynyl, which are unsubstituted, or substituted by $R^{91}$; $C_3$-$C_6$-cycloalkyl, $C_3$-$C_6$-halocycloalkyl, which cyclic groups are unsubstituted, or substituted by $R^{92}$; or heterocyclyl, or hetaryl, which rings are unsubstituted, or substituted by $R^D$;

Usually, $R^{11}$ is H. In another embodiment, $R^{11}$ is $C_1$-$C_6$-alkyl-$C(=O)$, $C_1$-$C_6$-haloalkyl-$C(=O)$, $C_1$-$C_6$-alkyl-$OC(=O)$, $C_1$-$C_6$-alkenyl-$OC(=O)$, or $C_6$-$C_{12}$-aryl-$C_1$-$C_6$-alkyl-$OC(=O)$.

In another embodiment, $R^8$ is $C_1$-$C_6$-alkyl-$OC(=O)$, $C_1$-$C_6$-alkenyl-$OC(=O)$, or $C_6$-$C_{12}$-aryl-$C_1$-$C_6$-alkyl-$OC(=O)$, in particular Boc, Fmoc, $CH_3C(=O)$, Alloc, Cbz, and especially Boc, Fmoc, Alloc, and Cbz.

Usually, compounds of formula I are according to compounds of formula I-A

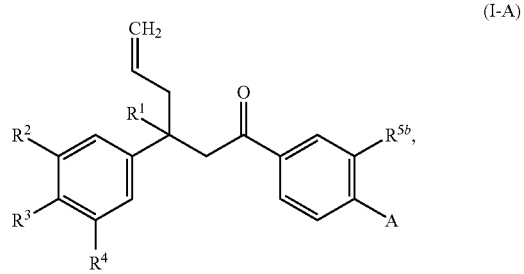

(I-A)

wherein all substituents have a meaning as defined for compounds of formula I.

Preferably, the invention relates to compounds of formula I-B

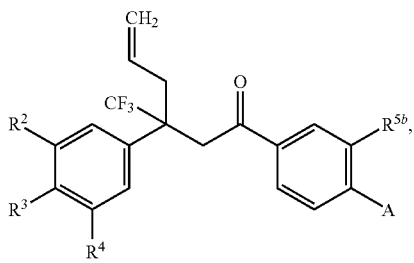
(I-A)

wherein all substituents have a meaning as defined for compounds of formula I.

Usually, compounds of formula II, III, and IV have a substitution pattern as in compounds of formula I-B.

Usually, compounds of formula II are according to compounds of formula II-A

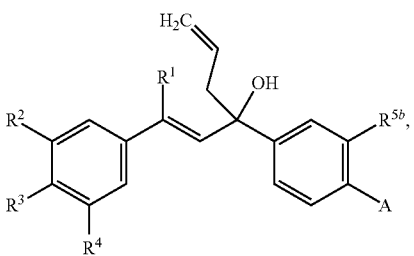
(II-A)

wherein all substituents are as defined for compounds of formula I.

Preferably, compounds of formula II are according to compounds of formula II-B

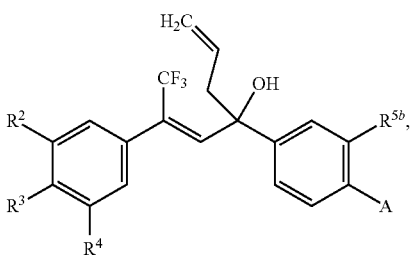
(II-B)

wherein all substituents are as defined for compounds of formula I.

Usually, compounds of formula III are according to compounds of formula III-A

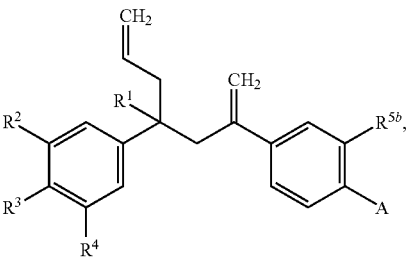
(III-A)

wherein all substituents are as defined for formula I.

Preferably, compounds of formula III are according to compounds of formula III-B

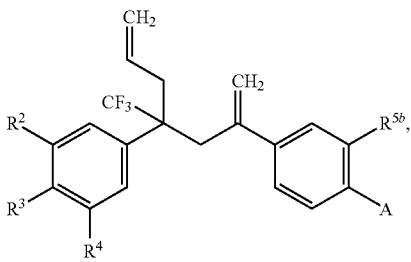
(III-B)

wherein all substituents are as defined for compounds of formula I.

Usually, compounds of formula IV are according to compounds of formula IV-A

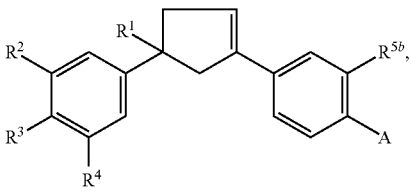
(IV-A)

wherein all substituents are as defined for compounds of formula I.

Preferably, compounds of formula IV are according to compounds of formula IV-B

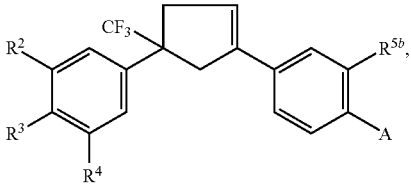
(IV-B)

wherein all substituents are as defined for compounds of formula I.

In particular, the meaning of the substituents in compounds of formula I-A, I-B, II-A, II-B, III-A, III-B, IV-A, or IV-B have independently, and under the condition that they are present or not defined otherwise, the following meaning:

$R^1$ is trihalomethyl;
$R^2$ is halogen, halomethyl, or halomethoxy;
$R^3$, $R^4$ are independently H, or as defined for $R^2$;
$R^{5b}$ is halogen, methyl, or halomethyl;
and A has a meaning as defined for compounds of formula I.

In particular, A is C(=O)NHR$^9$; wherein
$R^9$ is H;
  $C_1$-$C_6$-alkyl, $C_2$-$C_6$-alkenyl, $C_2$-$C_6$-alkynyl, which are unsubstituted, or substituted by $R^{91}$;
  $C_3$-$C_6$-cycloalkyl, $C_3$-$C_6$-halocycloalkyl, wherein the cyclic groups are unsubstituted, or substituted by $R^{92}$;
  NR$^{93}$R$^{94}$; or
  phenyl, heterocycyclyl, or hetaryl, which are unsubstituted, or substituted by R$^D$;
$R^{91}$ halogen, OH, CN, $C_1$-$C_4$-alkoxy, $C_1$-$C_4$-haloalkoxy, $C_1$-$C_4$-alkyl-S(O)$_m$, $C_1$-$C_4$-haloalkyl-S(O)$_m$, C(=O)N(R$^A$)R$^B$;

$C_3$-$C_6$-cycloalkyl, $C_3$-$C_6$-halocycloalkyl, which groups are unsubstituted, or substituted by $R^C$;

phenyl, heterocyclyl, or hetaryl which rings are unsubstituted, or substituted by $R^D$;

$R^A$, $R^{93}$ H, $C_1$-$C_3$-alkyl, or $C_1$-$C_3$-haloalkyl;

$R^B$ H, $C_1$-$C_3$-alkyl, $C_1$-$C_3$-haloalkyl, $C_2$-$C_3$-alkenyl, $C_2$-$C_3$-haloalkenyl, $C_2$-$C_3$-alkynyl, $C_2$-$C_3$-haloalkynyl, $C_1$-$C_3$-alkoxy, $C_1$-$C_3$-haloalkoxy, $C_3$-$C_4$-cycloalkyl, $C_3$-$C_4$-halocycloalkyl; or $C_3$-$C_4$-cycloalkylmethyl, $C_3$-$C_4$-halocycloalkylmethyl, wherein the cyclic groups are unsubstituted, or substituted by CN;

$R^C$ OH, CN, $C_1$-$C_2$-alkyl, or $C_1$-$C_2$-haloalkyl;

$R^D$ halogen, CN, $NO_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_4$-cycloalkylmethyl, or $C_3$-$C_4$-halocycloalkylmethyl;

$R^{92}$ $C_1$-$C_2$-alkyl, $C_1$-$C_2$-haloalkyl, or a group as defined for $R^{91}$;

$R^{94}$ $C(=O)N(R^A)R^B$, $C(=O)OR^A$; or phenyl, heterocyclyl, or hetaryl which rings are unsubstituted, or substituted by $R^D$;

n is 0, or 1;

m is 0, 1, or 2;

and the N-oxides, stereoisomers and agriculturally or veterinarily acceptable salts thereof.

In one embodiment, $R^9$ is a) H;

b) $C_1$-$C_6$-alkyl, $C_2$-$C_6$-alkenyl, which groups are unsubstituted, or substituted by $R^{91}$;

c) $C_3$-$C_6$-cycloalkyl, $C_3$-$C_6$-halocycloalkyl, which groups are unsubstituted, or substituted by $R^{92}$; or d) phenyl, heterocyclyl, or hetaryl, which are unsubstituted, or substituted by $R^D$.

In another embodiment, $R^9$ is H. In another embodiment, $R^9$ is $C_1$-$C_6$-alkyl, $C_2$-$C_6$-alkenyl, which groups are unsubstituted, or substituted by $R^{91}$. In another embodiment, $R^9$ is $C_3$-$C_6$-cycloalkyl, $C_3$-$C_6$-halocycloalkyl, which groups are unsubstituted, or substituted by $R^{92}$. In yet another embodiment, $R^9$ is phenyl, heterocyclyl, or hetaryl, which are unsubstituted, or substituted by $R^D$.

In one embodiment, $R^{91}$ is a) halogen, CN, $C_1$-$C_4$-alkoxy, $C_1$-$C_4$-haloalkoxy, $C_1$-$C_4$-alkyl-$S(O)_m$, $C_1$-$C_4$-haloalkyl-$S(O)_m$, $C(=O)NHR^B$;

b) $C_3$-$C_6$-cycloalkyl, $C_3$-$C_6$-halocycloalkyl, which groups are unsubstituted, or substituted by $R^C$;

c) phenyl, heterocyclyl, or hetaryl, which are unsubstituted, or substituted by $R^D$.

In another embodiment, $R^{91}$ is halogen, CN, $C_1$-$C_4$-alkoxy, $C_1$-$C_4$-haloalkoxy, $C_1$-$C_4$-alkyl-$S(O)_m$, $C_1$-$C_4$-haloalkyl-$S(O)_m$, $C(=O)NHR^B$. In another embodiment, $R^{91}$ is $C_3$-$C_6$-cycloalkyl, $C_3$-$C_6$-halocycloalkyl, which groups are unsubstituted, or substituted by $R^C$. In another embodiment, $R^{91}$ is phenyl, heterocyclyl, or hetaryl, which are unsubstituted, or substituted by $R^D$.

In one embodiment $R^C$ is CN, $C_1$-$C_2$-alkyl, or $C_1$-$C_2$-haloalkyl. In another embodiment, $R^C$ is CN, $CH_3$, or halomethyl. In another embodiment, $R^C$ is $CF_3$. In another embodiment, $R^C$ is $CH_3$. In another embodiment, $R^C$ is CN.

In one embodiment, $R^D$ is halogen, CN, $C_1$-$C_4$-alkyl, $C_1$-$C_4$-haloalkyl, $C_3$-$C_6$-cycloalkyl, $C_3$-$C_6$-halocycloalkyl, $C_3$-$C_4$-cycloalkylmethyl, or $C_3$-$C_4$-halocycloalkylmethyl. In another embodiment, $R^D$ is selected from halogen. In another embodiment, $R^D$ is selected $C_1$-$C_4$-alkyl. In another embodiment, $R^D$ is selected $C_1$-$C_4$-haloalkyl.

In one embodiment, the meaning of the substituents in compounds of formula I-A, I-B, II-A, II-B, III-B, IV-A, or IV-B have independently, and under the condition that they are present or not defined otherwise, the following meaning:

$R^1$ is $CF_3$;

$R^2$ F, Cl, Br, $CF_3$, or $OCF_3$;

$R^3$ and $R^4$ are independently H, or as defined for $R^2$;

$R^{5b}$ F, Cl, Br, $CH_3$, or $CF_3$;

A $C(=O)NHR^9$;

$R^9$ H;

$C_1$-$C_6$-alkyl, $C_2$-$C_6$-alkynyl, which groups are unsubstituted, or substituted by $R^{91}$;

$C_3$-$C_6$-cycloalkyl, $C_3$-$C_6$-halocycloalkyl, which cyclic groups are unsubstituted, or substituted by $R^{92}$; or heterocyclyl, or hetaryl which rings are unsubstituted, or substituted by $R^D$;

$R^{91}$ halogen, CN, $C_1$-$C_4$-alkoxy, $C_1$-$C_4$-haloalkoxy, $C_1$-$C_4$-alkyl-$S(O)_m$, $C_1$-$C_4$-haloalkyl-$S(O)_m$, $C(=O)NHR^B$;

$C_3$-$C_6$-cycloalkyl, $C_3$-$C_6$-halocycloalkyl, which groups are unsubstituted, or substituted by $R^C$;

heterocyclyl, or hetaryl which rings are unsubstituted, or substituted by $R^D$;

$R^A$ H, $C_1$-$C_3$-alkyl, or $C_1$-$C_3$-haloalkyl;

$R^B$ H, $C_1$-$C_3$-alkyl, $C_1$-$C_3$-haloalkyl, $C_2$-$C_3$-alkenyl, $C_2$-$C_3$-haloalkenyl, $C_2$-$C_3$-alkynyl, $C_2$-$C_3$-haloalkynyl, $C_1$-$C_3$-alkoxy, $C_1$-$C_3$-haloalkoxy, $C_3$-$C_4$-cycloalkyl, $C_3$-$C_4$-halocycloalkyl; or $C_3$-$C_4$-cycloalkylmethyl, $C_3$-$C_4$-halocycloalkylmethyl, wherein the cyclic groups are unsubstituted, or substituted by CN;

$R^C$ CN, $C_1$-$C_2$-alkyl, or $C_1$-$C_2$-haloalkyl;

$R^D$ halogen, CN, $NO_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_4$-cycloalkylmethyl, or $C_3$-$C_4$-halocycloalkylmethyl;

$R^{92}$ $C_1$-$C_2$-alkyl, $C_1$-$C_2$-haloalkyl, or a group as defined for $R^{91}$;

n is 0, or 1;

m is 0, 1, or 2;

and the N-oxides, stereoisomers and agriculturally or veterinarily acceptable salts thereof.

In one embodiment, $R^9$ and/or $R^{91}$ are independently phenyl, pyridyl, i.e. 2-, 3-, and 4-pyridyl, pyrimidinyl, i.e. 2-, 4- and 5-pyrimidinyl, pyrazinyl, pyridazinyl, i.e. 3- and 4-pyridazinyl, 2- and 3-thietanyl, 2- and 3-thietanyl-S-oxide (S-oxothietanyl), 2- and 3-thietanyl-S-dioxide (S-dioxothiethanyl), or 2-isoxazolidinyl.

In another embodiment, $R^9$ and/or $R^{91}$ are independently pyridyl, i.e. 2-, 3-, and 4-pyridyl, pyrimidinyl, i.e. 2-, 4- and 5-pyrimidinyl, pyrazinyl, pyridazinyl, i.e. 3- and 4-pyridazinyl, 2- and 3-thietanyl, 2- and 3-thietanyl-S-oxide (S-oxothietanyl), 2- and 3-thietanyl-S-dioxide (S-dioxothiethanyl), or 2-isoxazolidinyl.

In another embodiment, $R^9$ and/or $R^{91}$ are independently phenyl.

The following examples illustrate the invention.

EXAMPLES

I. Characterization

The characterization can be done by coupled High Performance Liquid Chromatography/mass spectrometry (HPLC/MS), by NMR or by their melting points. HPLC/MS. The gradient for HPLC/MS was 5-100% B in 1.5 min, 100% B for 0.2 min (0.8-1.0 mL/min flow rate). Mobile phase A was water, mobile phase B was MeCN (acetonitrile). Column temperature was 60° C. The column used for the chromatography was a UPLC Phenomenex Kinetex column with 1.7 µm XB-C18 100 A and dimensions of 50×2.1 mm. MS-method: ESI positive.

Abbreviations used are: h for hour(s), min for minute(s), eq for equivalent(s). Abbreviations used for NMR are: s for singlet, d for doublet, t for triplet, q for quartet, dd for doublet of doublets, dt for doublet of triplets, qd for quartet of doublets, ddd for doublet of doublets of doublets, m for multiplet, J for coupling constant, H for the integrated intensity of one hydrogen atom, Hz is Hertz.

PREPARATION EXAMPLES

Example 1: Preparation of 4-(4-bromophenyl)-6-(3,5-dichlorophenyl)-7,7,7-trifluoro-hepta-1,5-dien-4-ol (Compound II.1)

To 1-(4-bromophenyl)-3-(3,5-dichlorophenyl)-4,4,4-trifluoro-but-2-en-1-one (5.5 g) in anhydrous THF (30 mL) was added allylmagnesium chloride (1.43 g) in diethylether (13 mL) at 0° C. under argon atmosphere. The resulting mixture was stirred at 0° C. for 2 h. Saturated aqueous $NH_4Cl$-solution (15 mL) was then added to the mixture, which was subsequently stirred for 15 min. The phases were separated and the aqueous phase was extracted with ethyl acetate. The combined organic phases were dried and concentrated in vacuo. Compound II.1 was isolated from the residue by silica column chromatography with a yield of 96%. LC-MS: mass found 463.1; retention time 1.400 min.

Chemical shift of compound II.1 in $^1$H NMR (400 MHz, $CDCl_3$) 7.46-7.39 (d, J=8.7 Hz, 2H), 7.29 (t, J=1.8 Hz, 1H), 7.13-7.05 (d, J=8.7 Hz, 2H), 6.84 (d, J=1.9 Hz, 2H), 6.77 (q, J=1.6 Hz, 1H), 5.60 (ddt, J=17.5, 10.3, 7.3 Hz, 1H), 5.33-5.13 (m, 2H), 2.68-2.67 (d, J=7.4 Hz, 2H)

Example 2: Preparation of 1-(4-bromophenyl)-3-(3,5-dichlorophenyl)-3-(trifluoromethyl)hex-5-en-1-one (Compound I.1)

A mixture of potassium hexamethyldisilazide (KHMDS, 0.371 g), and 18-crown-6 ether (0.25 g) in toluene (10.8 mL) was produced. A solution of compound II.1 of Example 1 (0.400 g) in toluene (2.5 mL) was added at −78° C. to the mixture. The resulting mixture was stirred at −78° C. for 10 min, and then stirred for another 30 min at 20 to 25° C. An aqueous saturated $NaHCO_3$ solution (20 mL) was added to the mixture, followed by addition of an aqueous saturated $NH_4Cl$ solution (100 mL). The mixture was then extracted with ethyl acetate. The organic extracts were combined and concentrated in vacuo. Compound I.1 was isolated from the residue by silica column chromatography with a yield of 75%. LC-MS: mass found 466.9; retention time 1.592 min.

Example 3: Preparation of 1-[1-allyl-3-(4-bromophenyl)-1-(trifluoromethyl)but-3-enyl]-3,5-dichloro-benzene (Compound III.1)

To a stirred suspension of methyltriphenylphosphonium bromide (0.506 g) in THF (5 mL) was added potassium tert-butanolate (0.144 g) portion wise at 20 to 25° C., and the resulting mixture was stirred at 20 to 25° C. for 30 min. To this mixture was added compound I.1 (0.3 g) of Example 2 in THF (2 mL) at 0° C. The mixture was stirred over night at 20 to 25° C., upon which water was added. The mixture was subsequently extracted with ethyl acetate. The combined organic phases were dried and concentrated in vacuo. Compound III.1 was isolated from the residue by silica column chromatography with a yield of 80%. LC-MS: mass found 466.9; retention time 1.648 min.

Chemical shifts of compound III.1 in $^1$H NMR (400 MHz, $CDCl_3$) 7.37-7.27 (m, 4H), 7.18-7.12 (m, 3H), 6.97-6.90 (m, 2H), 5.78-5.56 (m, 1H), 5.24 (d, J=1.1 Hz, 1H), 5.18-5.04 (m, 2H), 5.00 (q, J=1.1 Hz, 1H), 3.16 (dd, J=14.6, 1.2 Hz, 1H), 3.02 (dd, J=14.6, 0.9 Hz, 1H), 2.84 (dd, J=15.5, 6.2 Hz, 1H), 2.64 (dd, J=15.6, 7.7 Hz, 1H).

Example 4: Preparation of 1-[3-(4-bromophenyl)-1-(trifluoromethyl)cyclopent-3-en-1-yl]-3,5-dichloro-benzene (Compound IV.1)

To a solution of (1,3-bis(2,4,6-trimethylphenyl)-2-imidazolidinylidene)dichloro-(phenylmethylene)(tricyclohexylphosphine)ruthenium (15.5 mg) in $CH_2Cl_2$ (3.5 mL) was added compound III.1 of Example 3 (0.17 g) at 20 to 25° C. under argon. The resulting mixture was stirred for 3 h at 20 to 25° C. The solvent was evaporated in vacuo. Compound IV.1 was isolated from the residue by silica column chromatography with a yield of 63%. LC-MS: no mass observed; retention time 1.7 min.

Chemical shifts of compound IV.1 in $^1$H NMR (400 MHz, $CDCl_3$) δ 7.48 (d, J=8.6 Hz, 2H), 7.36-7.27 (m, 5H), 6.15 (s, 1H), 3.50 (d, J=16.5 Hz, 1H), 3.35 (d, J=17.9 Hz, 1H), 3.24 (dd, J=16.5, 2.4 Hz, 1H), 3.08 (dd, J=18.0, 2.5 Hz, 1H).

Example 5: Preparation of methyl 4-[1-allyl-3-(3-chloro-4-fluoro-phenyl)-4,4,4-trifluoro-1-hydroxy-but-2-enyl]-2-chloro-benzoate (Compound II.2)

To a mixture of methyl 2-chloro-4-[3-(3-chloro-4-fluoro-phenyl)-4,4,4-trifluoro-but-2-enoyl]benzoate (0.25 g) in DMF (5 mL) was added zinc dust (0.194 g) and allyl bromide (0.215 g) at 0° C. The resulting mixture was stirred for 2 h at 0° C., and then stirred for 48 h at 20 to 25° C. Solids particles were removed from the mixture by filtration. To the filtrate was added saturated aqueous $NH_4Cl$-solution (25 mL) and water (25 mL). The aqueous phase was then extracted with ethyl acetate. The combined organic phases were washed, dried and concentrated in vacuo. Compound II.2 was isolated from the residue by silica column chromatography with a yield of 91%. LC-MS: mass found 463.1; retention time 1.380 min.

Example 6: Preparation of methyl 2-chloro-4-[3-(3-chloro-4-fluoro-phenyl)-3-(trifluoromethyl)hex-5-enoyl]benzoate (Compound I.2)

To a solution of KHMDS (2.239 g) and 18-crown-6-ether (2.51 g) in toluene (95.6 mL) was added compound II.2 of Example 5 (5 g) in toluene (15 mL) at −78° C. The resulting mixture was stirred at −78° C. for 10 min. The mixture was then stirred for 30 min at 20 to 25° C. The mixture was then diluted with an aqueous saturated solution of $NaHCO_3$ (50 mL), followed by a saturated aqueous solution of $NH_4Cl$ (100 mL). The mixture was then extracted with ethyl acetate. The combined organic phases were washed, dried and concentrated in vacuo. Compound I.2 was isolated from the residue by silica column chromatography with a yield of 95%.

Chemical shifts of compound I.2 in $^1$H NMR (400 MHz, $CDCl_3$) 7.94 (s, 1H), 7.89 (dd, J=8.1, 1.5 Hz, 1H), 7.81 (d, J=8.1 Hz, 1H), 7.44 (d, J=6.8 Hz, 1H), 7.32-7.04 (m, 4H), 5.85 (dt, J=16.4, 8.3 Hz, 1H), 5.23-4.89 (m, 2H), 3.97 (s, 3H), 3.83 (d, J=18.5 Hz, 1H), 3.65 (dd, J=18.5, 1.5 Hz, 1H), 3.17 (qd, J=14.3, 7.3 Hz, 2H).

Example 7: Preparation of methyl 2-chloro-4-[3-(3-chloro-4-fluoro-phenyl)-1-methylene-3-(trifluoromethyl)hex-5-enyl]benzoate (Compound III.2)

A suspension of methyltriphenylphosphonium bromide (0.506 g) in toluene (50 mL) was concentrated in vacuo three times. THF (4 mL) was added to the resulting residue, which was subsequently cooled to 0° C. A mixture of KHMDS (0.258 g) in THF (1.3 mL) was then added dropwise. The resulting mixture was then stirred for 30 min, upon which a solution of compound I.2 of Example 6 (0.3 g) in THF (2 mL) was admixed.

The mixture was then stirred at 20 to 25° C. for 18 h. Subsequently, water (50 mL) and ethyl acetate (50 mL) were added to the mixture. The organic layer was separated, and the aqueous layer was extracted with ethyl acetate. The combined organic phases were washed, dried and concentrated in vacuo. Compound III.2 was isolated from the residue by silica column chromatography with a yield of 30%.

Chemical shifts of compound III.2 in $^1$H NMR (400 MHz, CDCl$_3$) 7.69 (d, J=8.2 Hz, 1H), 7.32 (dd, J=6.9, 2.5 Hz, 1H), 7.21 (ddd, J=8.9, 4.4, 2.6 Hz, 1H), 7.13 (d, J=1.8 Hz, 1H), 7.04 (dd, J=8.2, 1.8 Hz, 1H), 6.98 (t, J=8.7 Hz, 1H), 5.82-5.53 (m, 1H), 5.32 (d, J=0.9 Hz, 1H), 5.17-5.03 (m, 3H), 3.93 (s, 3H), 3.18 (dd, J=14.7, 1.2 Hz, 1H), 3.10-3.01 (m, 1H), 2.91-2.7 (m, 1H), 2.67 (dd, J=15.6, 7.6 Hz, 1H).

Example 8: Preparation of methyl 2-chloro-4-[4-(3-chloro-4-fluoro-phenyl)-4-(trifluoromethyl)cyclopenten-1-yl]benzoate (Compound IV.2)

To a solution of (1,3-bis(2,4,6-trimethylphenyl)-2-imidazolidinylidene)dichloro(phenylmethylene)(tricyclohexylphosphine)ruthenium (1 mg) in CH$_2$Cl$_2$ (1.5 mL) was added compound III.2 of Example 7 (75 mg) at 20 to 25° C. under argon. The resulting mixture was stirred for 5 h at 20 to 25° C. The solvent was evaporated in vacuo. Compound IV.2 was isolated from the residue by silica column chromatography with a yield of 57%.

Chemical shifts of compound IV.2 in $^1$H NMR (400 MHz, CDCl$_3$) 7.85 (d, J=8.2 Hz, 1H), 7.48 (dd, J=6.7, 2.1 Hz, 2H), 7.37 (dd, J=8.1, 1.7 Hz, 1H), 7.32 (ddd, J=7.2, 4.1, 2.5 Hz, 1H), 7.15 (t, J=8.7 Hz, 1H), 6.30 (d, J=2.3 Hz, 1H), 3.93 (s, 3H), 3.53 (dd, J=16.3, 1.4 Hz, 1H), 3.40 (d, J=18.2 Hz, 1H), 3.28 (dd, J=16.3, 2.4 Hz, 1H), 3.14 (dd, J=18.2, 2.6 Hz, 1H).

Example 9: Preparation of 1-(4-bromophenyl)-3-(3,5-dichloro-4-fluoro-phenyl)-3-(trifluoromethyl)hex-5-en-1-one (Compound I.3)

To a solution of KHMDS (151 mg) and 18-crown-6-ether (120 mg) in THF (5 mL) was added 4-(4-bromophenyl)-6-(3,5-dichloro-4-fluoro-phenyl)-7,7,7-trifluoro-hepta-1,5-dien-4-ol (200 mg, prepared analogously to Example 5) in THF (1 mL) at −78° C. The resulting mixture was stirred at −78° C. for 10 min. The mixture was then stirred for 30 min at 20 to 25° C. The mixture was then diluted with an aqueous saturated solution of NaHCO$_3$ (10 mL), followed by a saturated aqueous solution of NH$_4$Cl (10 mL). The mixture was then extracted with ethyl acetate. The combined organic phases were washed, dried and concentrated in vacuo. Compound I.3 was isolated from the residue by silica column chromatography with a yield of 68%.

1H NMR (400 MHz, Chloroform-d) δ 7.76 (d, J=8.6 Hz, 2H), 7.61 (d, J=8.6 Hz, 2H), 7.28 (s, 2H), 5.84 (m, 1H), 5.07 (m, 2H), 3.79 (d, J=18.4 Hz, 1H), 3.65 (d, J=18.4 Hz, 1H), 3.17 (m, 2H).

Example 10: Preparation of 1-(4-bromophenyl)-3-(3,5-dichloro-4-fluoro-phenyl)-3-(trifluoromethyl)hex-5-en-1-one (Compound I.3)

To a solution consisting of KHMDS (134 mg), toluene (0.95 mL), 18-crown-6-ether (90 mg) and xylenes (2.5 mL) was added 4-(4-bromophenyl)-6-(3,5-dichloro-4-fluorophenyl)-7,7,7-trifluoro-hepta-1,5-dien-4-ol (150 mg, prepared analogously to Example 5) in xylenes (1 mL) at −40° C. The resulting mixture was stirred at −40° C. for 10 min. The mixture was then stirred for 30 min at 20 to 25° C. The mixture was then diluted with an aqueous saturated solution of NaHCO$_3$ (10 mL), followed by a saturated aqueous solution of NH$_4$Cl (10 mL). The mixture was then extracted with ethyl acetate. The combined organic phases were washed, dried and concentrated in vacuo. Compound I.3 was isolated from the residue by silica column chromatography with a yield of 60%.

Example 11: Preparation of 1-(4-bromophenyl)-3-(3,5-dichloro-4-fluoro-phenyl)-3-(trifluoromethyl)hex-5-en-1-one (Compound I.3)

To a solution consisting of KHMDS (134 mg), toluene (0.95 mL), 18-crown-6-ether (90 mg), and 1,4-dioxane (2.5 mL) was added 4-(4-bromophenyl)-6-(3,5-dichloro-4-fluorophenyl)-7,7,7-trifluoro-hepta-1,5-dien-4-ol (150 mg, prepared analogously to Example 5) in 1,4-dioxane (1 mL) at −78° C. The resulting mixture was stirred at −78° C. for 10 min. The mixture was then stirred for 30 min at 20 to 25° C. The mixture was then diluted with an aqueous saturated solution of NaHCO$_3$ (10 mL), followed by a saturated aqueous solution of NH$_4$Cl (10 mL). The mixture was then extracted with ethyl acetate. The combined organic phases were washed, dried and concentrated in vacuo. Compound I.3 was isolated from the residue by silica column chromatography with a yield of 59%.

Example 12: Preparation of methyl 2-chloro-4-[3-(3-chloro-4-fluoro-phenyl)-3-(trifluoromethyl)hex-5-enoyl]benzoate (Compound I.2)

To a solution of KOtBu (26.4 g) and 18-crown-6-ether (62.26 g) in THF (290 mL) at 0° C. was added compound II.2 of Example 5 (46.2 g) in THF (430 mL) at −25° C. to −20° C. The resulting mixture was stirred at −20° C. for 30 min. The mixture was then stirred for 15 min at 0° C. Water (1 L) was added to the mixture, the layers were separated and the organic layer was washed with water three times. The organic phase was dried and concentrated in vacuo. Compound I.2 was isolated from the residue by silica column chromatography with a yield of 64%.

Chemical shifts of compound I.2 in $^1$H NMR (400 MHz, CDCl$_3$) 7.94 (s, 1H), 7.89 (dd, J=8.1, 1.5 Hz, 1H), 7.81 (d, J=8.1 Hz, 1H), 7.44 (d, J=6.8 Hz, 1H), 7.32-7.04 (m, 4H), 5.85 (dt, J=16.4, 8.3 Hz, 1H), 5.23-4.89 (m, 2H), 3.97 (s, 3H), 3.83 (d, J=18.5 Hz, 1H), 3.65 (dd, J=18.5, 1.5 Hz, 1H), 3.17 (qd, J=14.3, 7.3 Hz, 2H).

Example 13: Preparation of 1-(4-bromo-3-chloro-phenyl)-3-(3,5-dichloro-4-fluorophenyl)-3-(trifluoromethyl)hex-5-en-1-one (Compound I.4)

To a suspension of NaH (11 mg of a 60% mineral oil suspension) and 18-crown-6-ether (75 mg) in THF (5 mL)

was added 4-(4-bromo-3-chlorophenyl)-6-(3,5-dichloro-4-fluoro-phenyl)-7,7,7-trifluoro-hepta-1,5-dien-4-ol (prepared analogously to example 5) (130 mg) in THF (1 mL) at −78° C. The resulting mixture was stirred at −78° C. for 1 h. The mixture was then stirred for 30 min at 20 to 25° C. The mixture was then diluted with an aqueous saturated solution of NaHCO₃ (10 mL), followed by a saturated aqueous solution of NH₄Cl (10 mL). The mixture was then extracted with ethyl acetate. The combined organic phases were washed, dried and concentrated in vacuo. Compound I.4 was isolated from the residue by silica column chromatography with a yield of 30%. 1H NMR (500 MHz, Chloroform-d) δ 7.96 (d, J=2.1 Hz, 1H), 7.75 (d, J=8.3 Hz, 1H), 7.63 (dd, J=8.4, 2.1 Hz, 1H), 7.34 (d, J=5.9 Hz, 2H), 6.14-5.72 (m, 1H), 5.32-4.85 (m, 2H), 3.75 (d, J=18.5 Hz, 1H), 3.64 (d, J=18.5 Hz, 1H). 3.14 (m, 2H).

The invention claimed is:

1. A compound of formula I

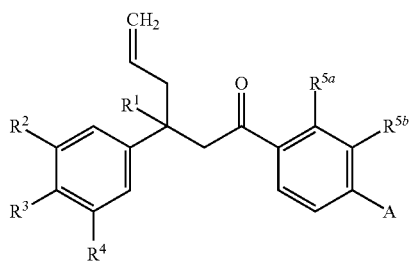

(I)

wherein
$R^1$ is halomethyl;
$R^2$ is halogen, halomethyl, or halomethoxy;
$R^3$, $R^4$ are independently H, or as defined for $R^2$;
$R^{5a}$ is H, $C_1$-$C_4$-alkyl, or $C_1$-$C_4$-haloalkyl;
$R^{5b}$ is CN, halogen, $C_1$-$C_2$-alkyl, $C_1$-$C_2$-haloalkyl, $C_1$-$C_2$-alkoxy, $C_1$-$C_2$-haloalkoxy; or
$R^{5a}$ and $R^{5b}$ form together with the C-atoms they are bound to a 5-, or 6-membered saturated, partially, or fully unsaturated ring containing none, or one heteroatom O, $N(O)_n$ or $S(O)_m$ as ring members;
A is halogen, CN, $C_1$-$C_6$-alkoxy, $C_6$-$C_{10}$-aryloxy, $C_1$-$C_6$-haloalkoxy, $C_6$-$C_{10}$-arylalkoxy, $C_6$-$C_{10}$-aryl-$C_1$-$C_6$-alkoxy, $OS(O)_2R^6$; or
a group $A^1$, or $A^2$; wherein
$A^1$ is a group of following formula:

(A¹)

wherein
# denotes the attachment point to the remainder of the molecule;
Y $OR^7$, or $N(R^8)R^9$; and
$A^2$ is a group of following formula:

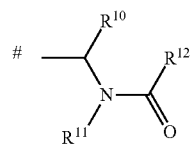

(A²)

wherein
# denotes the attachment point to the remainder of the molecule;
$R^6$ halogen, $C_1$-$C_6$-alkyl, $C_1$-$C_6$-haloalkyl;
phenyl, which is unsubstituted, or substituted by halogen, OH, CN, NO₂, $C_1$-$C_6$-alkyl, or $C_1$-$C_6$-haloalkyl;
$R^7$ a) H;
b) $C_1$-$C_6$-alkyl, $C_1$-$C_6$-haloalkyl, $C_1$-$C_6$-alkenyl, $C_1$-$C_6$-alkynyl, $C_1$-$C_6$-alkoxy-$C_1$-$C_6$-alkyl; or
c) phenyl, or benzyl, which are unsubstituted, or substituted by halogen, $C_1$-$C_2$-alkyl, $C_1$-$C_2$-haloalkyl, or $C_1$-$C_2$-alkoxy;
$R^8$ H, CN;
$C_1$-$C_6$-alkyl-C(=O), $C_1$-$C_6$-haloalkyl-C(=O), $C_1$-$C_6$-alkyl-OC(=O), $C_1$-$C_6$-alkenyl-OC(=O), or $C_6$-$C_{12}$-aryl-$C_1$-$C_6$-alkyl-OC(=O);
$C_1$-$C_{10}$-alkyl, $C_3$-$C_8$-cycloalkyl, $C_2$-$C_{10}$-alkenyl, $C_2$-$C_{10}$-alkynyl, which are unsubstituted or substituted by $R^{81}$;
$R^{81}$ halogen, CN, N₃, NO₂, SCN, SF₅, $C_3$-$C_8$-cycloalkyl, $C_3$-$C_8$ halocycloalkyl, $C_1$-$C_6$-alkoxy, $C_1$-$C_6$-haloalkoxy, $C_3$-$C_8$-cycloalkoxy, or $C_3$-$C_8$-halocycloalkoxy;
$R^9$ H;
$C_1$-$C_6$-alkyl, $C_2$-$C_6$-alkenyl, $C_2$-$C_6$-alkynyl, which are unsubstituted, or substituted by $R^{91}$;
$C_3$-$C_6$-cycloalkyl, $C_3$-$C_6$-halocycloalkyl, which are unsubstituted, or substituted by $R^{92}$;
$N(R^{93})R^{94}$;
phenyl, heterocyclyl, or hetaryl, which are unsubstituted, or substituted by $R^D$; or
$C_1$-$C_6$-alkyl-C(=O), $C_1$-$C_6$-haloalkyl-C(=O), $C_1$-$C_6$-alkyl-OC(=O), $C_1$-$C_6$-alkenyl-OC(=O), or $C_6$-$C_{12}$-aryl-$C_1$-$C_6$-alkyl-OC(=O);
$R^{91}$ halogen, OH, CN, $C_1$-$C_4$-alkoxy, $C_1$-$C_4$-haloalkoxy, $C_1$-$C_4$-alkyl-$S(O)_m$, $C_1$-$C_4$-haloalkyl-$S(O)_m$, C(=O)N($R^A$)$R^B$;
$C_3$-$C_6$-cycloalkyl, $C_3$-$C_6$-halocycloalkyl, which are unsubstituted, or substituted by $R^C$;
phenyl, heterocyclyl, or hetaryl which are unsubstituted, or substituted by $R^D$;
$R^A$, $R^{93}$ H, $C_1$-$C_3$-alkyl, or $C_1$-$C_3$-haloalkyl;
$R^B$ H, $C_1$-$C_3$-alkyl, $C_1$-$C_3$-haloalkyl, $C_2$-$C_3$-alkenyl, $C_2$-$C_3$-haloalkenyl, $C_2$-$C_3$-alkynyl, $C_2$-$C_3$-haloalkynyl, $C_1$-$C_3$-alkoxy, $C_1$-$C_3$-haloalkoxy, $C_3$-$C_4$-halocycloalkyl; or
$C_3$-$C_4$-cycloalkyl, $C_3$-$C_4$-halocycloalkyl, $C_3$-$C_4$-cycloalkylmethyl, $C_3$-$C_4$-halocycloalkylmethyl, wherein the cyclic groups are unsubstituted, or substituted by CN;
$R^C$ OH, CN, $C_1$-$C_2$-alkyl, or $C_1$-$C_2$-haloalkyl;
$R^D$ halogen, CN, NO₂, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_4$-cycloalkylmethyl, or $C_3$-$C_4$-halocycloalkylmethyl; or
two $R^D$ present on the same carbon atom of a saturated, or partially saturated ring form together a carbonyl group (=O);
$R^{92}$ $C_1$-$C_2$-alkyl, $C_1$-$C_2$-haloalkyl, or a group as defined for $R^{91}$;
$R^{94}$ C(=O)N($R^A$)$R^B$, C(=O)$OR^A$; or
phenyl, heterocyclyl, or hetaryl which rings are unsubstituted, or substituted by $R^D$;
$R^{10}$ H, CN, methyl, or halomethyl;
$R^{11}$ H, $C_1$-$C_6$-alkyl-C(=O), $C_1$-$C_6$-haloalkyl-C(=O), $C_1$-$C_6$-alkyl-OC(=O), $C_1$-$C_6$-alkenyl-OC(=O), or $C_6$-$C_{12}$-aryl-$C_1$-$C_6$-alkyl-OC(=O);
$R^{12}$ H, $C_1$-$C_6$-alkyl, $C_2$-$C_6$-alkenyl, $C_2$-$C_6$-alkynyl, which are unsubstituted, or substituted by $R^{91}$;

C$_3$-C$_6$-cycloalkyl, C$_3$-C$_6$-halocycloalkyl, which are unsubstituted, or substituted by R$^{92}$; or phenyl, heterocycyl, or hetaryl which rings are unsubstituted, or substituted by R$^D$;

n is 0, or 1;

m is 0, 1, or 2;

and the N-oxides, stereoisomers and agriculturally or veterinarily acceptable salts thereof.

2. The compound of claim 1, wherein

R$^1$ is CF$_3$;

R$^2$ is F, Cl, Br, CF$_3$, or OCF$_3$;

R$^3$, R$^4$ are independently H, or as defined for R$^2$;

R$^{5a}$ is H; and

R$^{5b}$ is F, Cl, Br, CH$_3$, or CF$_3$; or

R$^{5a}$ and R$^{5b}$ form together with the C-atoms they are bound to a bridging group selected from —CH=CH—CH=CH—, —CH=CH—CH=N—, —CH=CH—N=CH—, —CH=N—CH=CH—, —N=CH—CH=CH—, —CH$_2$CH$_2$CH$_2$—, —CH$_2$CH$_2$CH$_2$CH$_2$—, —CH$_2$CH$_2$O—, —OCH$_2$CH$_2$—, —CH$_2$CH$_2$CH$_2$O—, —OCH$_2$CH$_2$CH$_2$—, —CH$_2$CH$_2$S(O)$_p$—, —S(O)$_p$CH$_2$CH$_2$—;

and wherein p is 0, 1, or 2.

3. The compound of claim 1, wherein

A is A$^1$;

Y is OR$^7$; and

R$^7$ is as defined in claim 1.

4. The compound of claim 3, wherein R$^7$ is C$_1$-C$_6$-alkyl, C$_1$-C$_6$-haloalkyl, C$_1$-C$_6$-alkenyl, C$_1$-C$_6$-alkynyl, phenyl, or benzyl.

5. The compound of claim 2, wherein

A is A$^1$;

Y is N(H)R$^9$.

6. The compound of claim 1, wherein A is Cl, Br, I, or CN.

7. The compound of claim 1, wherein

A is A$^2$;

R$^{10}$ H; and

R$^{12}$ C$_1$-C$_4$-alkyl, and C$_1$-C$_4$-haloalkyl, which are unsubstituted, or substituted by R$^{91}$;

C$_3$-C$_5$-cycloalkyl, C$_3$-C$_5$-halocycloalkyl, which are unsubstituted, or substituted by R$^{92}$;

R$^{91}$ is independently OH, CN, C$_1$-C$_4$-alkoxy, C$_1$-C$_4$-haloalkoxy, C$_1$-C$_4$-alkyl-S(O)$_m$, C$_1$-C$_4$-haloalkyl-S(O)$_m$;

C$_3$-C$_5$-cycloalkyl, C$_3$-C$_5$-halocycloalkyl, which are unsubstituted, or substituted by R$^C$;

R$^C$ is independently OH, CN, C$_1$-C$_2$-alkyl, or C$_1$-C$_2$-haloalkyl;

R$^{92}$ is independently C$_1$-C$_4$-alkyl, C$_1$-C$_4$-haloalkyl, or a group as defined for R$^{91}$; and m is 0, 1, or 2.

8. A process for preparing the compound of claim 1 comprising reacting a compound of formula II

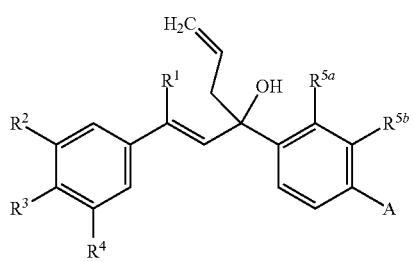

with a base at a temperature from −100 to 50° C., followed by rearrangement at a temperature from −50 to 150° C.

9. The process of claim 8, wherein the reaction of the compound of formula (II) with the base is carried out in a solvent selected from the selected from an aliphatic C$_5$-C$_{16}$-hydrocarbon, aromatic C$_6$-C$_{10}$-hydrocarbon, halogenated aliphatic C$_1$-C$_6$-hydrocarbon, halogenated aromatic C$_6$-C$_{10}$-hydrocarbon, a C$_1$-C$_6$-cycloalkyl ether, a C$_1$-C$_6$-alkyl-C$_1$-C$_6$-alkyl ether, and a C$_1$-C$_6$-alkyl-C$_6$-C$_{10}$-aryl ether, or a mixture thereof.

10. The process of claim 8, wherein the rearrangement is carried out at a temperature from −10 to 40° C.

11. The process of claim 8, wherein compound of formula I are subsequently reacted with an olefinating agent to compound of formula III

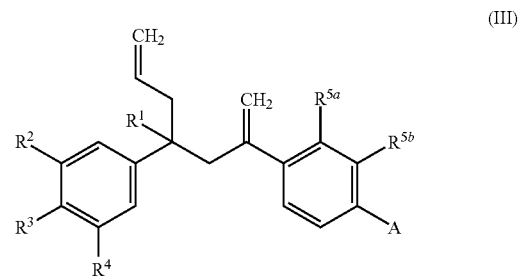

wherein all substituents have a meaning as defined for compound of formula I.

12. The process of claim 11, wherein the olefinating agent is selected from methylphosphonium ylides, Tebbe's reagent, Petasis reagent, Lombardo reagent, or Kauffmann reagent.

13. The process of claim 8, wherein compound of formula III are subsequently reacted to compound of formula IV

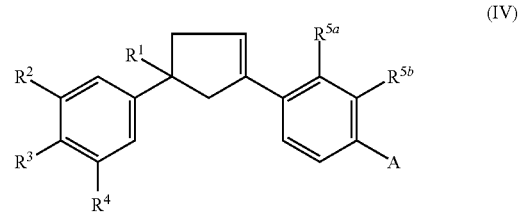

in the presence of an alkylidene-metal catalyst; wherein all substituents have a meaning as defined for compound of formula I.

14. The process of claim 13, wherein the metal is selected from W, Ta, Mo, and Ru.

15. The process of claim 8, wherein compound of formula II are produced by reaction of compound of formula V

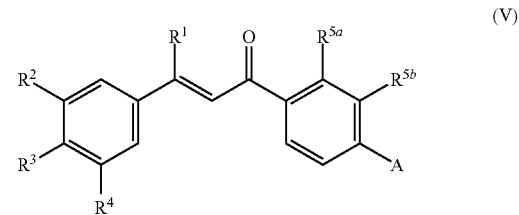

with an allylation reagent;
wherein all substituents have a meaning as defined for compound of formula I.
16. Compound of formula II, as defined in claim 8.
17. Compound of formula III, as defined in claim 11.
18. A process for preparing the compound of formula IV

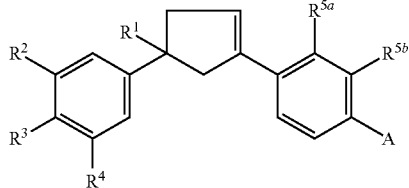

(IV)

comprising reacting a compound of formula III

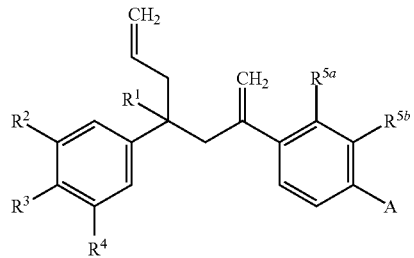

(III)

in the presence of an alkylidene-metal catalyst, as defined in claim 13.

* * * * *